US006605037B1

(12) United States Patent
Moll et al.

(10) Patent No.: US 6,605,037 B1
(45) Date of Patent: *Aug. 12, 2003

(54) ENDOSCOPIC INFLATABLE RETRACTION DEVICE

(75) Inventors: Frederic H. Moll, San Francisco, CA (US); Charles Gresl, Jr., San Francisco, CA (US); Albert K. Chin, Palo Alto, CA (US); Philip K. Hopper, Laverne, CA (US)

(73) Assignee: Sherwood Services AG, Schaffhausen (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/179,008

(22) Filed: Oct. 26, 1998

Related U.S. Application Data

(63) Continuation of application No. 08/561,160, filed on Nov. 21, 1995, now Pat. No. 5,865,728, which is a continuation-in-part of application No. 08/106,231, filed on Aug. 13, 1993, now abandoned, which is a division of application No. 07/794,590, filed on Nov. 19, 1991, now Pat. No. 5,309,896, which is a continuation-in-part of application No. 07/706,781, filed on May 29, 1991, now abandoned.

(51) Int. Cl.[7] .............................................. A61B 17/02

(52) U.S. Cl. ................... 600/204; 600/207; 604/101.02

(58) Field of Search ................................ 606/192, 198; 600/204, 205, 207; 604/101.02

(56) References Cited

U.S. PATENT DOCUMENTS

| 1,060,250 A | 4/1913 | Ginaca |
| 1,275,520 A | 8/1918 | Bell |

(List continued on next page.)

FOREIGN PATENT DOCUMENTS

| DE | 502 331 | 3/1939 |
| DE | 28 47 633 | 5/1979 |
| EP | 0 010 650 | 5/1980 |
| EP | 0 246 086 | 11/1987 |
| EP | 0 251 976 | 1/1988 |
| EP | 0 275 230 A2 | 7/1988 |
| EP | 0 411 767 A1 | 2/1991 |
| FR | 2 474 304 | 7/1981 |
| FR | 2 646 088 | 10/1990 |
| FR | 2 688 695 | 9/1993 |
| GB | 2 071 502 | 9/1981 |
| WO | WO 91/01687 | 2/1991 |

*Primary Examiner*—Michael H. Thaler

(57) ABSTRACT

An inflatable retraction apparatus is provided for retracing an organ inside a body to gain access to an adjacent tissue. The apparatus includes an able chamber formed from a single thin envelope, and capable of being collapsed for insertion through an incision and being expanded to a predetermined shape for retracing the organ. An inflation mechanism is adapted to selectively inflate the chamber to the predetermined shape. The inflation mechanism includes at least one inflation tube attached to the inflatable chamber in fluid communication therewith, and an inflatable maintaining lattice operatively enveloping the inflatable chamber and in operative association with the inflation mechanism. The inflatable maintaining lattice defines a plurality of single layered access windows around the inflatable chamber, and is configured and adapted to maintain the inflatable chamber in substantially the predetermined shape after an aperture is pierced in at least one of the plurality of access windows of the inflatable chamber.

25 Claims, 20 Drawing Sheets

U.S. PATENT DOCUMENTS

| | | | |
|---|---|---|---|
| 1,735,519 A | 11/1929 | Vance | |
| 1,947,649 A | 2/1934 | Kadavy | |
| 2,663,020 A | 12/1953 | Cushman | |
| 2,854,983 A | 10/1958 | Baskin | |
| 3,039,468 A | 6/1962 | Price | |
| 3,173,418 A | 3/1965 | Baran | |
| 3,626,949 A | 12/1971 | Shute | |
| 3,774,596 A | * 11/1973 | Cook | |
| 3,782,370 A | 1/1974 | McDonald | |
| 3,800,788 A | 4/1974 | White | |
| 3,817,251 A | 6/1974 | Hasson | |
| 3,831,587 A | 8/1974 | Boyd | |
| 3,863,639 A | 2/1975 | Kleaveland | |
| 3,882,852 A | 5/1975 | Sinnreich | |
| 3,961,632 A | 6/1976 | Moossun | |
| 4,077,412 A | 3/1978 | Moossun | |
| 4,083,369 A | 4/1978 | Sinnreich | |
| 4,137,906 A | 2/1979 | Akiyama et al. | |
| 4,157,085 A | 6/1979 | Austad | |
| 4,183,102 A | * 1/1980 | Guiset | |
| 4,198,981 A | 4/1980 | Sinnreich | |
| 4,217,889 A | 8/1980 | Radovan et al. | |
| 4,240,433 A | 12/1980 | Bordow | |
| 4,254,762 A | 3/1981 | Yoon | |
| 4,263,900 A | 4/1981 | Nicholson | |
| 4,271,839 A | 6/1981 | Fogarty et al. | |
| 4,291,687 A | 9/1981 | Sinnreich | |
| 4,318,410 A | 3/1982 | Chin | |
| 4,357,940 A | 11/1982 | Muller | |
| 4,430,076 A | 2/1984 | Harris | |
| 4,447,227 A | 5/1984 | Kotsanis | |
| 4,493,711 A | 1/1985 | Chin et al. | |
| 4,517,979 A | 5/1985 | Pecenka | |
| 4,535,773 A | 8/1985 | Yoon | |
| 4,574,780 A | 3/1986 | Manders | |
| 4,598,699 A | 7/1986 | Garren et al. | |
| 4,601,710 A | 7/1986 | Moll | |
| 4,612,938 A | 9/1986 | Dietrich et al. | |
| 4,615,704 A | 10/1986 | Frisch | |
| 4,648,383 A | 3/1987 | Angelchik | |
| 4,651,717 A | 3/1987 | Jakubczak | |
| 4,654,030 A | 3/1987 | Moll et al. | |
| 4,666,447 A | 5/1987 | Smith et al. | |
| 4,709,697 A | 12/1987 | Muller | |
| 4,719,918 A | 1/1988 | Bonomo et al. | |
| 4,723,549 A | 2/1988 | Wholey et al. | |
| 4,739,762 A | 4/1988 | Palmaz | |
| 4,763,653 A | 8/1988 | Rockey | |
| 4,775,371 A | 10/1988 | Mueller, Jr. | |
| 4,779,611 A | 10/1988 | Grooters et al. | |
| 4,800,901 A | 1/1989 | Rosenberg | |
| 4,803,029 A | 2/1989 | Iversen et al. | |
| 4,863,440 A | 9/1989 | Chin | |
| 4,878,495 A | * 11/1989 | Grayzel | |
| 4,919,152 A | 4/1990 | Ger | |
| 4,944,443 A | 7/1990 | Oddsen et al. | |
| 4,966,583 A | 10/1990 | Debbas | |
| 4,976,710 A | 12/1990 | Mackin | |
| 4,984,564 A | 1/1991 | Yuen | |
| 5,002,557 A | 3/1991 | Hasson | |
| 5,007,898 A | 4/1991 | Rosenbluth et al. | |
| 5,049,132 A | 9/1991 | Shaffer et al. | |
| 5,082,005 A | 1/1992 | Kaldany | |
| 5,083,576 A | 1/1992 | Ruiz-Razura et al. | |
| 5,084,061 A | 1/1992 | Gau et al. | |
| 5,103,804 A | 4/1992 | Abele et al. | |
| 5,109,875 A | 5/1992 | Gottlieb | |
| 5,116,357 A | 5/1992 | Eberbach | |
| 5,122,122 A | 6/1992 | Allgood | |
| 5,158,548 A | 10/1992 | Lau et al. | |
| 5,163,949 A | 11/1992 | Bonutti | |
| 5,176,697 A | 1/1993 | Hasson et al. | |
| 5,178,133 A | 1/1993 | Pena | |
| 5,183,464 A | 2/1993 | Dubrul et al. | |
| 5,183,468 A | 2/1993 | McLees | |
| 5,188,596 A | 2/1993 | Condon et al. | |
| 5,188,630 A | 2/1993 | Christoudias | |
| 5,195,507 A | 3/1993 | Bilweis | |
| 5,197,948 A | 3/1993 | Ghodsian | |
| 5,197,971 A | * 3/1993 | Bonutti | 606/192 |
| 5,275,610 A | 1/1994 | Eberbach | |
| 5,331,975 A | 7/1994 | Bonutti | |

\* cited by examiner

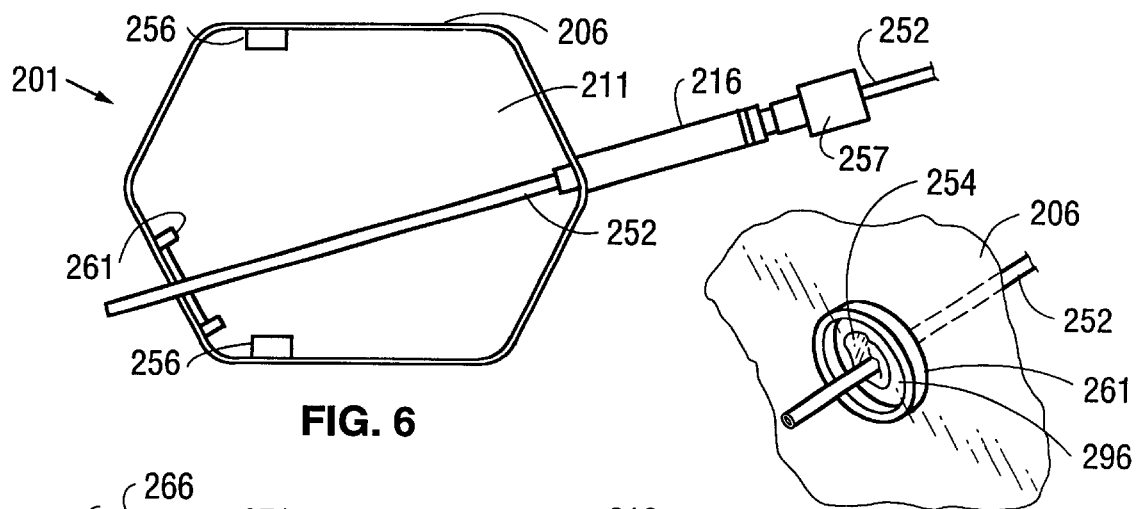
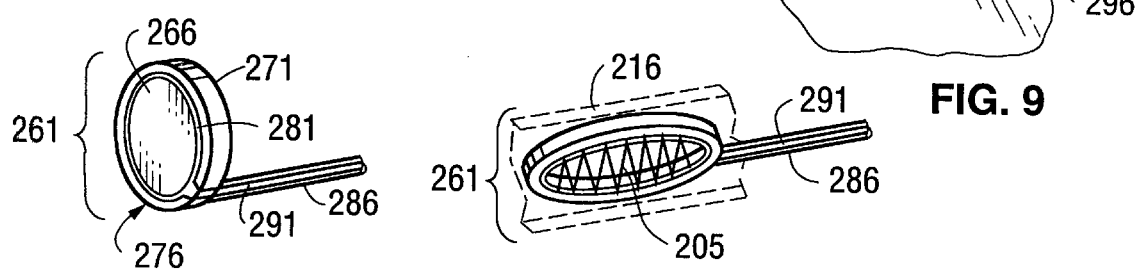
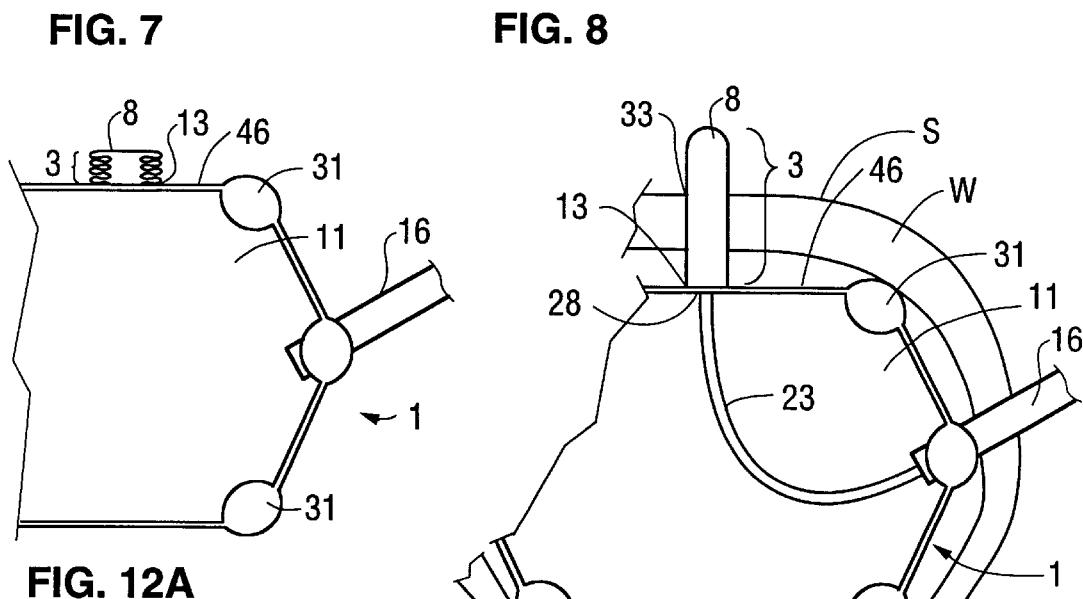

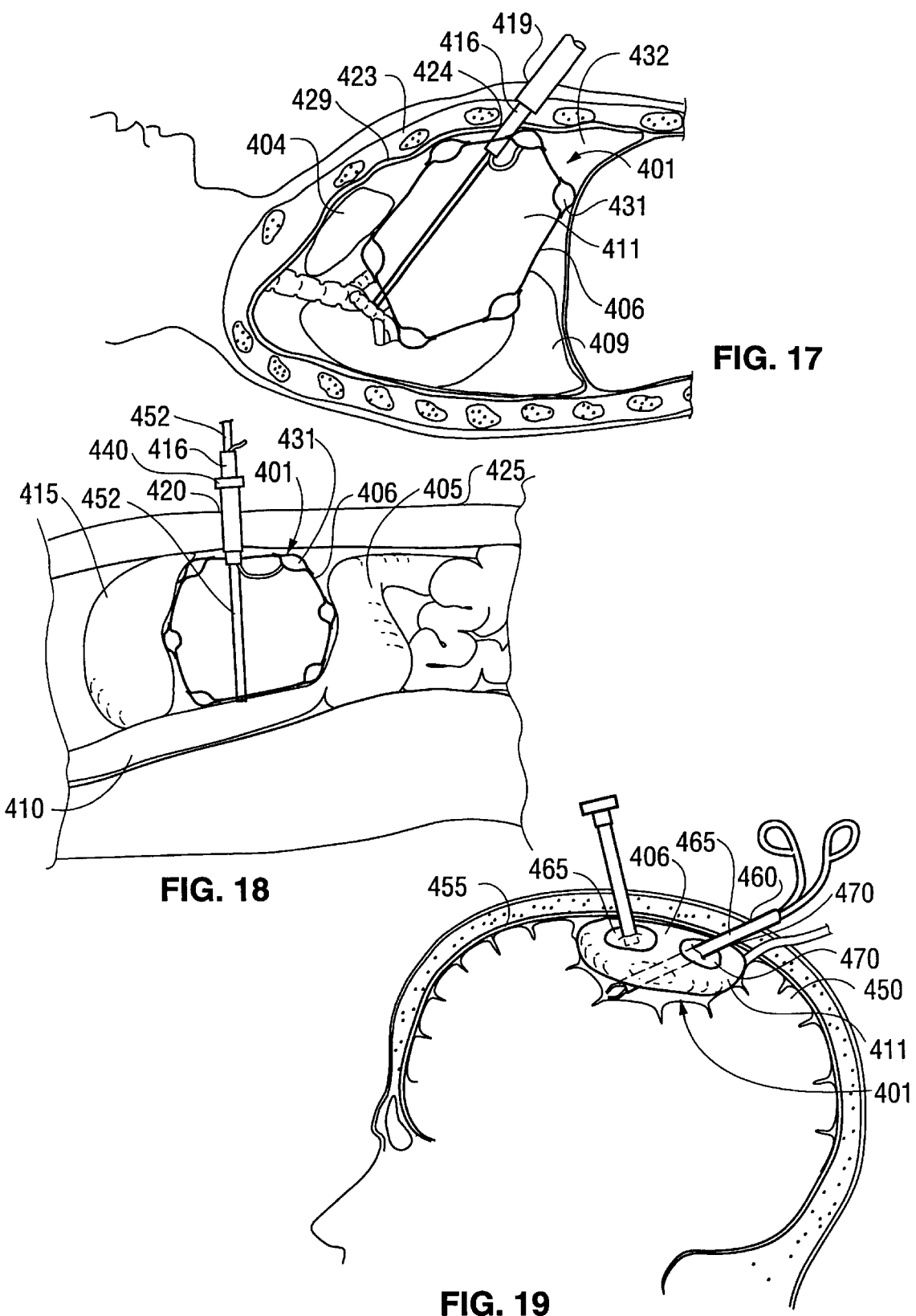

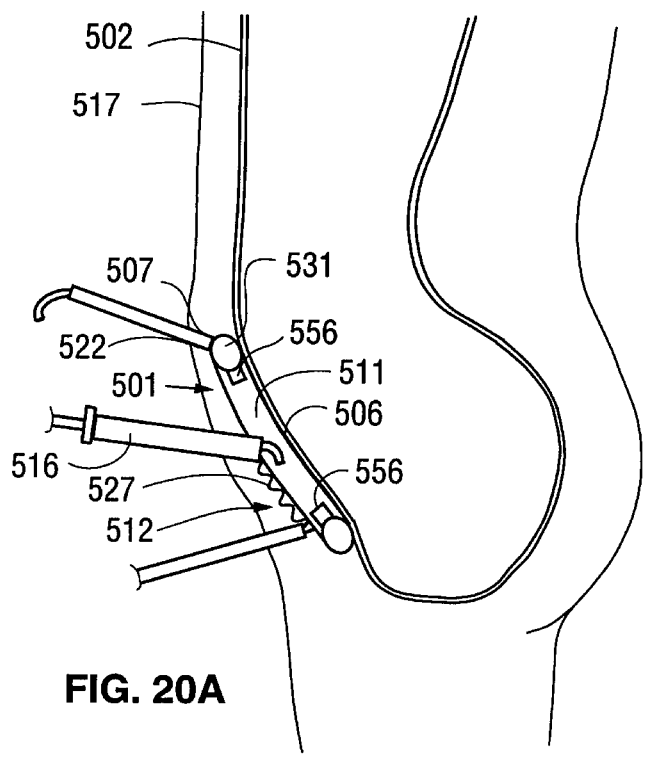
FIG. 20A
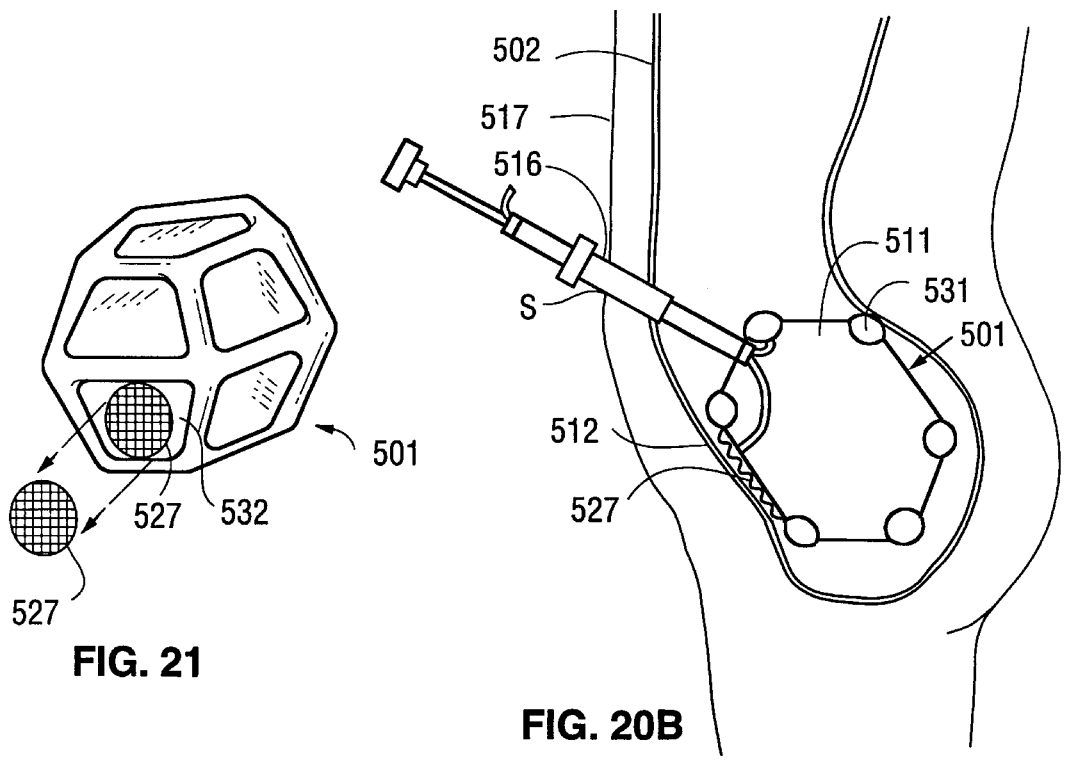
FIG. 21
FIG. 20B

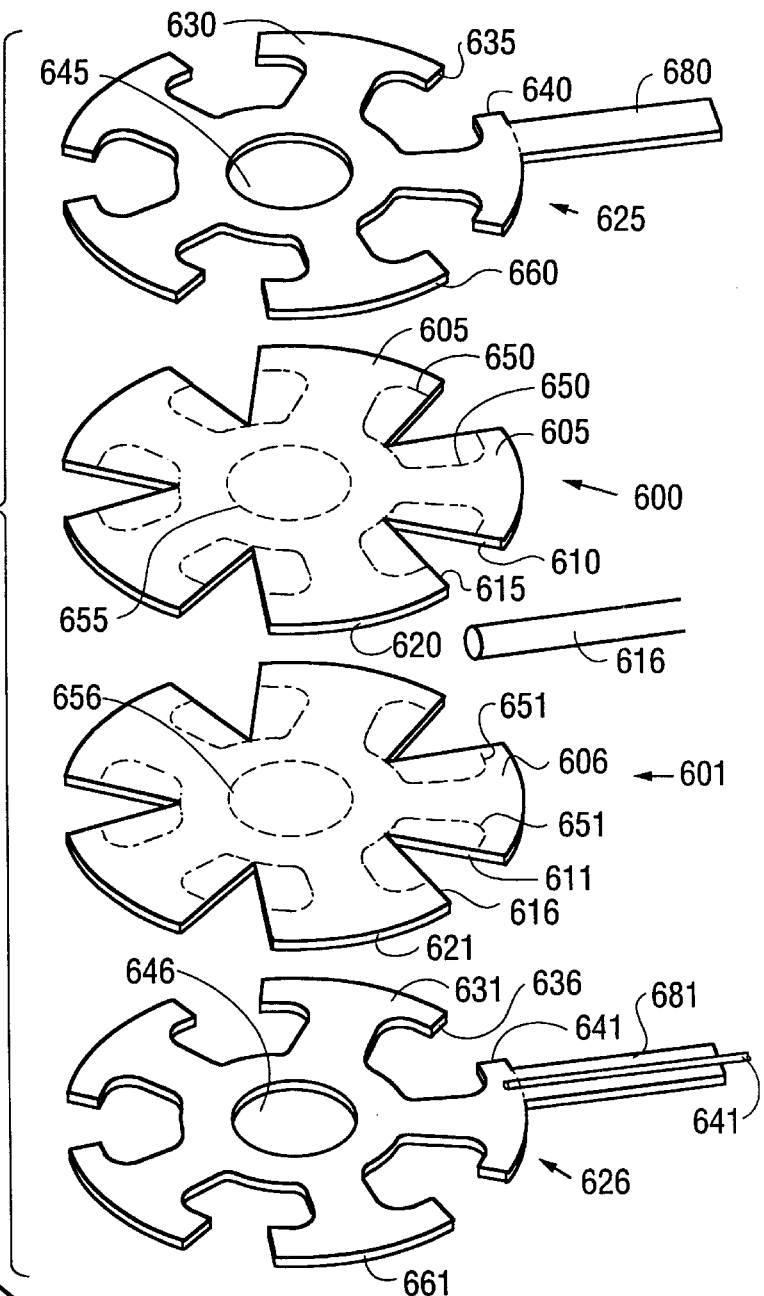
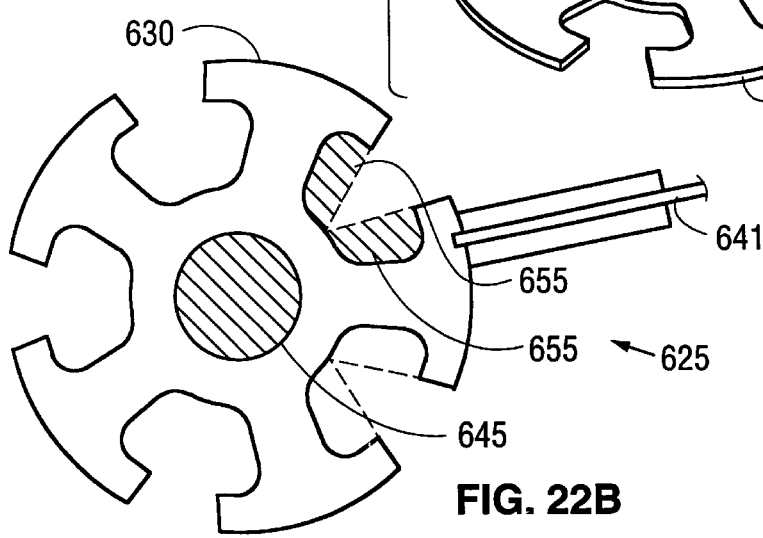
FIG. 22A
FIG. 22B

ENDOSCOPIC INFLATABLE RETRACTION DEVICE

This is a continuation of application Ser. No. 08/561,160, filed Nov 21, 1995 now U.S. Pat. No. 5,865,728 which is a continuation-in-part of application Ser. No. 08/106,231 filed Aug. 13, 1993 (now abandoned) which is a divisional of application Ser. No. 07/794,590 filed Nov. 19, 1991 (U.S. Pat. No. 5,309,896 issued May 10, 1994) which is a continuation-in-part of application Ser. No. 07/706,781 filed May 29, 1991 (now abandoned).

BACKGROUND OF THE INVENTION

Laparoscopy dates back to the turn of the 20th Century. Early laparoscopic techniques were used primarily for diagnostic purposes to view the internal organs, without the necessity of conventional surgery. Since the 1930s, laparoscopy has been used for sterilization and, more recently, for the suturing of hernias. U.S. Pat. Nos. 4,919,152 and 4,944,443 are concerned with techniques for suturing hernias. Another very recent innovation is the use of laparoscopic surgery for removing the gallbladder.

U.S. patent application Ser. No. 706,781, the application of which this application is a Continuation-in-Part, describes an apparatus and method wherein the abdominal wall is lifted away from the underlying abdominal organs by an inflatable device which is introduced laparoscopically and, once in place, inflated to engage and lift an extensive area of the abdominal wall.

Even when such lifting techniques are used, it is still necessary to retract other organs to gain access to the organ or tissue to be treated or observed. In other procedures, to gain access to the organ or tissue to be treated or observed, it is necessary to separate the organ to be treated from tissue surrounding it. For example, to be able to observe the outer surface the heart, the outer surface of the heart has to be separated from the pericardium. To obtain the necessary retraction, current laparoscopic procedures use several small retractors inserted though a plurality of incisions. Because such retractors have a relatively small surface area, they tend to damage and/or cause trauma to the retracted organs or tissue. Moreover, the requirement for a plurality of incisions to heal may delay the patient's recovery.

It is known to use a modified Foley catheter to retract organs and tissue with less damage. The modified Foley catheter comprises a small, substantially spherical balloon on the end of a catheter which is inserted through a small incision into the body. After insertion, the balloon is inflated. The modified Foley catheter is used in a similar manner to a conventional retractor, but the retracted organ or tissue is contacted by the relatively large surface area of the balloon. Such a retractor reduces damage to retracted organs or tissues, but is inconvenient to use because it has to be kept in place by means of an external clamping arrangement, and its relatively large balloon tends to obstruct access to the site to be treated.

SUMMARY OF THE INVENTION

The present invention relates to an inflatable retraction device that mechanically retracts organs and tissues to provide access to treat or observe other organs or tissues. More specifically, the invention is concerned with a retraction device that retracts organs or tissues by means of an inflatable chamber. The retraction device is introduced laparoscopically in a collapsed state into the body and, once in place, inflated to engage an extensive area of the organ or tissue to be retracted, and to gently retract or displace the organ or tissue without damaging it. During laparoscopic treatment and observation procedures, a retraction device according to the invention retains its expanded condition, and hence its ability to provide retraction, while providing access for surgical instruments through itself to the organ or tissue being treated or observed, or allowing an organ or tissue to be brought inside itself for observation or treatment.

In the following description, the word "organ" will be used to mean an organ or a tissue that is retracted by the retraction device. The word "treat" will be used to mean both treat and observe, and the word "treatment" will be used to mean both treatment and observation. The word "tissue" or the phrase "tissue to be treated" will both be used to mean the organ or the tissue that is treated through or inside the retraction device.

To provide the large surface area required to retract organs gently, the inflatable retraction device according to the invention is relatively large. As a result, the retraction device is normally juxtaposed between the entry through which surgical instruments pass into the body and the tissue to be treated. An inflatable retraction device according to the invention avoids obstructing the access of surgical instruments to the tissue to be treated by providing one or more apertures in the envelope of the device. Such apertures allow instruments to pass into and out of the interior of the retraction device, or allow the tissue to be treated to enter the interior of the retraction device for treatment by instruments passed into the interior of the device. Treatment is thus carried out working through or inside the retraction device according to the invention.

In those procedures in which the tissue to be treated enters the interior of retraction device through an aperture, the material of the retraction device surrounding the aperture may form a seal around the tissue, isolating it from the body outside the retraction device. Treatment of the tissue is carried out inside the retraction device.

According to different aspects of the invention, inflatable retraction devices according to the invention employ different ways to retain their ability to provide retraction while providing access for surgical instruments to the tissue to be treated or observed. An inflatable retraction device according to one aspect of the invention, such a retraction device being designated generally as a Type I retraction device, maintains its ability to provide retraction by means of an additional inflatable chamber, which forms a cage structure inside or outside the main inflatable chamber. The additional inflatable chamber is normally inflated after the main inflatable chamber of the retraction device has been inflated, and the retraction device has produced its desired retraction effect. Such an additional inflatable chamber is smaller and less powerful than the main inflatable chamber. Inflating the additional chamber alone would not always produce sufficient force to provide the desired retraction of the organ. However, the inflated additional chamber provides enough force to maintain an organ that has been retracted by the more powerful main inflatable chamber in its retracted position. The additional inflatable chamber is thus able to maintain the retraction effect of the retraction device after the retraction effect of the main inflatable chamber has been destroyed by piercing an aperture in the envelope of the main chamber to provide access to the tissue to be treated.

The tube used to inflate the main chamber provides primary access for surgical instruments to the interior of the retraction device. If more instruments than can be accommodated by the inflation tube are needed, or if the inflation tube is not conveniently aligned with the tissue to be treated, instruments can additionally or alternatively be inserted through additional incisions. The instruments enter the retraction device through additional apertures in the envelope of the main chamber. The apertures are cut in the part of the envelope of the main chamber that does not form part of the additional inflatable chamber.

In an alternative embodiment of a retraction device according to the invention, the ability of the retraction device to provide a retraction effect during the treatment or observation procedure is maintained by keeping the main chamber of the retraction device in an inflated state during the treatment procedure. Such a retraction device, designated generally as a Type II retraction device, does not require an additional inflation chamber to maintain its retraction effect. An elastomeric window is attached to the inside of the retraction device after the device has been inflated. The elastomeric window provides a gas-tight seal around instruments passed through it, and around a tissue brought into the interior of the retraction device through it.

After the window has been installed, an instrument is passed through the window to pierce an aperture in the part of the envelope of the retraction device covered by the window to provide access to the organ to be treated. Surgical instruments are passed into the interior of the retraction device, primarily through the main inflation tube. The instruments can pass out of the retraction device to the tissue to be treated through the elastomeric window and the aperture in the envelope of the main chamber. Alternatively, the tissue to be treated enters the interior of the retraction device through the aperture and the elastomeric window. The elastomeric window provides a seal around the tissue to be treated enabling the retraction device to be maintained in its inflated state while treatment is carried out.

A Type I or a Type II retraction device according to the invention may be provided, according to a further aspect of the invention, with tabs attached to the interior surface of the envelope of the device. The tabs are gripped with a suitable gripping tool to adjust the position and orientation of the inflated retraction device relative to the tissue to be treated. The retraction device may be partially deflated to enable adjustments to be more easily made.

According to a further aspect of the invention, a Type I or a Type II retraction device may be provided, when in its collapsed state prior to inflation, with markings on its surface to aid proper orientation prior to inflation.

According to a further aspect of the invention, a Type I or a Type II retraction device according to the invention may further be provided with a flexible sheath for providing a port to allow surgical instruments to pass from outside the body to the main chamber of the retraction device. The interior of the flexible sheath communicates with the main chamber of the retraction device. The flexible sheath is deployed after the retraction device has been inflated. According to one aspect of this invention, a flexible sheath attached to the envelope of the retraction device driven outward through the body wall. According to an alternative aspect of this invention, the flexible sheath is driven inward through the body wall to pierce, and to lock into engagement with, the envelope of the retraction device.

According to a further aspect of the invention, in a retraction device according to the invention, the part of the envelope of the retraction device that is lower-most when the retraction device is deployed in the body is fitted with an integral tubular suction skirt. The suction skirt is connected to the operating room suction line and allows continuous or intermittent drainage of fluid that collects in the bottom of the cavity created by the retraction device during laparoscopic surgery.

An inflatable retraction device according to the method of the invention is used according to the invention by forming a small opening in the wall of the body and laparoscopically inserting the retraction device into the body in a contracted state. After insertion and orientation, the retraction device is inflated. During the inflation process, the relatively large surface area of the retraction device gently retracts the organ obstructing access to the tissue to be treated.

After the retraction device has been inflated, surgical instruments are passed from outside the body into the retraction device. One or more apertures are created by piercing, and possibly at least partially removing, the envelope of the retraction device adjacent to the tissue to be treated. The one or more apertures in the envelope of the retraction device provide access for the instruments to the tissue to be treated. Treatment is then carried out by working through the one or more apertures in the retraction device. The apertures may also provide access to the interior of the retraction device for surgical instruments passed from outside the body. Alternatively, the tissue to be treated can enter the main chamber of the retraction device through the one or more apertures and be treated inside the retraction device.

After the treatment has been completed, the retraction device is deflated and evacuated prior to its removal from the body in a collapsed state.

When a inflatable retraction device is used in the abdominal cavity, a inflatable retraction device according to the invention may be used alone to provide both retraction and lifting of the abdominal wall, or it may be used together with the abdominal lifting devices disclosed in the application Ser. No. 706,781, of which application this application is a Continuation-in-Part, or together with known insufflation techniques for lifting the abdomen.

The invention is also concerned with methods of using inflatable retraction devices according to the invention in new procedures for suturing hernias without breaching the peritoneum, anterior resection of herniated intervertebral discs, resecting the lung, lung lobectomies, and for procedures for observing or treating the heart, the brain, the esophagus, and the prostate.

The various procedures according to the invention involve placing an inflatable retraction device according to the invention inside a part of the body, such as the abdomen, the chest, or the skull via a small, limited incision or puncture site. The inflatable retraction device is placed adjacent to the organ to be displaced. Inflating the retraction device retracts the organ and exposes the tissue to be treated. Treatment of the tissue to be treated is then carried out using instruments passed into the interior of the retraction device. The tissue to be treated may remain outside the retraction device, or can enter the retraction device during treatment.

In a procedure according to the invention to repair a hernia by placing a mesh over the site of the hernia, an inflatable retraction device is used to provide retraction and, additionally, to hold the mesh in place over the site of the hernia while the mesh is stapled in place.

In a first method of construction according to the invention, a Type II polyhedral retraction device is made from suitably shaped pieces of flat plastic film connected together to form a polyhedral main envelope enclosing the main chamber. Such a construction can be used to approximate a spherical or spheroidal shape. A main inflation tube is attached to the main envelope such that the interior of the main inflation tube is in communication with the main chamber.

In a first method for constructing a polyhedral Type I retraction device, a segmented additional envelope is formed from suitably shaped pieces of flat plastic film. The pieces are shaped to provide the required cage structure of the additional chamber. The additional chamber is formed by attaching the periphery of the additional envelope to the outside or the inside of the main envelope. The part of the surface of the main envelope that is not covered by the additional envelope provides a plurality of windows, which, after the additional chamber is inflated, may be at least partially removed to provide apertures through which treatment or observation can be carried out. An additional inflation tube is attached to the additional envelope such that the interior of the additional inflation tube is in communication with the additional chamber.

In an alternative method of making an inflatable Type II retraction device according to the invention, two curved pieces of plastic film are attached to one another at their peripheries to form a main envelope enclosing a main chamber. A main inflation tube is attached to the main envelope such that the interior of the main inflation tube is in communication with the main chamber.

In an alternative method for constructing a Type I retraction device, an additional envelope is formed from two more pieces of curved plastic film shaped to form the required cage structure of the additional chamber. The two pieces of the additional envelope are attached to one another either outside or inside the main envelope. The additional chamber is formed by attaching the periphery of the additional envelope to the outside or the inside of the main envelope. The part of the surface of the main envelope that is not covered by the additional envelope provides a plurality of windows which, after the additional chamber is inflated, may be at least partially removed to provide apertures through which treatment or observation can be carried out. An additional inflation tube is attached to the additional envelope such that the interior of the additional inflation tube is in communication with the additional chamber.

BRIEF DESCRIPTION OF THE DRAWINGS

FIG. 6 is a perspective view of a polyhedral Type II inflatable retraction device according to a second embodiment of the invention showing an elastomeric window attached to the inner surface of its main envelope;

FIG. 7 is a perspective view of an elastomeric window suitable for attaching to the inner surface of the main envelope of a polyhedral Type II inflatable retraction device according to a second embodiment of the invention. The elastomeric window includes an electrical element for heating temperature sensitive adhesive applied to one of the surfaces of the elastomeric window.

FIG. 8 is a perspective view of the elastomeric window of FIG. 7 packaged prior to insertion into the retraction device.

FIG. 9 is a perspective view of the outer surface of the main envelope of a polyhedral Type II inflatable retraction device according to a second embodiment of the invention. An elastomeric window has been attached to the inside of the main envelope and an aperture has been cut in the part of the main envelope covered by the elastomeric window.

FIG. 12A is a vertical cross sectional view of a polyhedral inflatable retraction device according to the invention fitted with a first embodiment of flexible sheath according to the invention installed in the abdominal cavity with the flexible sheath in its collapsed state.

FIG. 12B is a vertical cross sectional view of a polyhedral inflatable retraction device according to the invention fitted with a first embodiment of flexible sheath according to the invention installed in the abdominal cavity showing the flexible sheath being driven through the abdominal wall.

FIG. 12C is a vertical cross sectional view of a window of a polyhedral inflatable retraction device according to the invention showing a second embodiment of a flexible sheath according to the invention.

FIG. 17 is a longitudinal cross sectional elevational view of the chest illustrating the use according to the invention of a retraction device according to the invention to retract one lobe of the lung away from the rest of the lung to gain access to occlude part of the bronchial tree during a lobectomy.

FIG. 18 is a longitudinal cross sectional elevational view of the abdomen illustrating the use according to the invention of a retraction device according to the invention to retract the liver to gain access to the gastroesophageal junction prior to sectioning the vagus nerve or to treating gastroesophageal reflux.

FIG. 19 is a longitudinal cross sectional elevational view of the head illustrating the use according to the invention of a retraction device according to the invention to retract the brain away from the dura mater to gain access to the brain for treatment or observation.

FIG. 20A is a transverse cross sectional elevational view of the lower abdomen illustrating the use according to the invention of a retraction device according to the invention between the abdominal wall and the peritoneum to retract the peritoneum to provide laparoscopic access to the site of a hernia without penetrating the peritoneum. A piece of mesh is shown being held in place over the site of the hernia by the retraction device.

FIG. 20B is a transverse cross sectional elevational view of the lower abdomen showing a retraction device according to the invention in its fully inflated condition holding a piece of mesh in position on the inside of the peritoneum over the site of the hernia.

FIG. 21 is a perspective view of a retraction device according to the invention with a piece of mesh attached to the outer surface of the main envelope.

FIG. 22A is an exploded perspective view of the components of a polygonal Type IA retraction device illustrating the construction of such a device according to the invention.

FIG. 22B is a plan view of the additional envelope blank of a polygonal Type IA retraction device.

DETAILED DESCRIPTION OF THE INVENTION

A. Inflatable Retraction Devices

1. Type IA Retraction Device—Basic Embodiment

Figure 1:
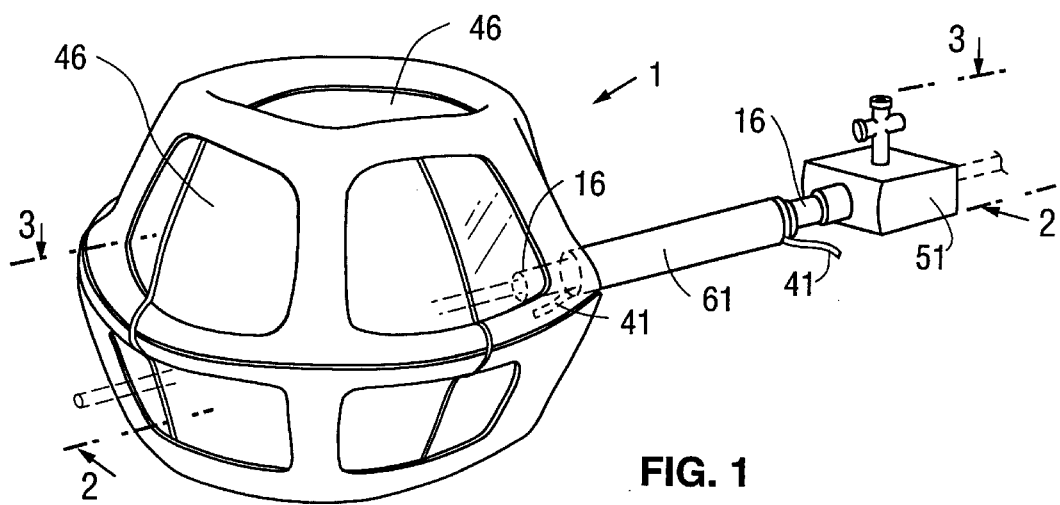
FIG. 1 is a perspective view of a polyhedral Type IA inflatable retraction device according to a first embodiment of the invention.
Figure 2:
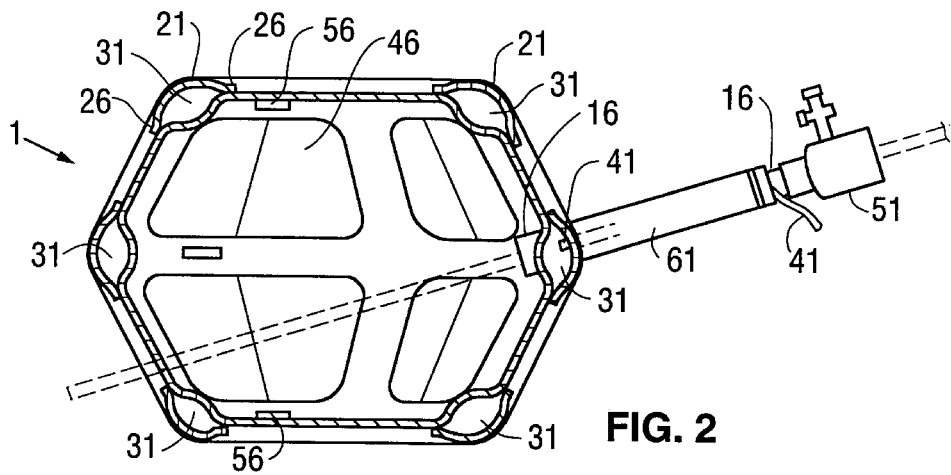
FIG. 2 is vertical cross section, along the line 2—2 in FIG. 1, of a polyhedral Type IA inflatable retraction device according to a first embodiment of the invention.
Figure 3:
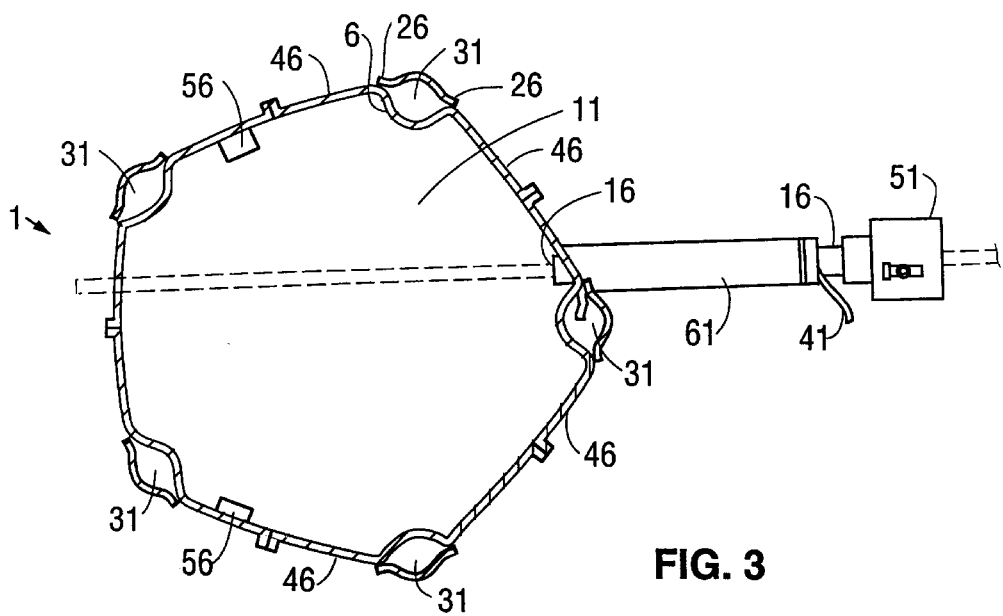
FIG. 3 is horizontal cross section, along the line 3—3 in FIG. 1, of a polyhedral Type IA inflatable retraction device according to a first embodiment of the invention.

FIGS. 1, 2, and 3 show perspective, and vertical and horizontal cross sectional views, respectively, of a first embodiment 1 of a retraction device according to the invention. This type of retraction device has an additional inflatable chamber and will be designated as a Type I retraction device. The Type I retraction device shown in FIGS. 1, 2, and 3 with a segmented additional chamber will be designated a Type IA retraction device. The retraction device is shown in its inflated condition. The retraction device 1 comprises a main envelope 6 enclosing a main inflatable chamber 11. The main envelope 6 is made of a relatively inelastic and tough film of a plastic such as Mylar®, polyethylene, or polyurethane. The preferred material for the main envelope 6 is a polyethylene and nylon composite. The thickness of the main envelope 6 is typically from 0.5 to 5 mils (13 to 130 microns). The proximal end of a main inflation tube 16 is sealed into the main envelope 6. The main inflation tube 16 allows an inflation gas to pass into and out of the main chamber 11. The inflation gas is typically air, nitrogen or carbon dioxide, although other suitable gases may be used. Typical inflation gas pressures are in the range 0.3 to 0.7 pounds per square inch (psi) (0.21 to 0.48 kPa), the preferred pressure being 0.5 psi (0.35 kPa). The main inflation tube 16 is provided with a port 51 on its distal end, through which endoscopes and/or surgical instruments can be passed into the main chamber 11. The port 51 allows the inflation pressure of the main chamber 11 to be maintained when surgical instruments are passed through the port.

The main envelope 6 of the Type IA retraction device is a polyhedral structure constructed from two segmented, substantially flat pieces of plastic film, which gives the retraction device a substantially polyhedral shape. Alternatively, two non-segmented, substantially flat pieces of plastic film can be used to make a relatively flat Type IA retraction device. In a further alternative, the retraction device can be constructed from curved pieces of plastic film, which gives the retraction device a substantially spherical, spheroidal, or ellipsoidal shape.

The size of retraction devices according to the invention can range from about 2" (50 mm) wide by about 0.5" (12 mm) high, for use inside the pericardium, to 10"–14" (250–350 mm) wide by 4"–8" (100–200 mm) high, for use in the abdominal cavity. The size of retraction device required for a given application depends on the application and the size of the patient.

In the preferred embodiment, the additional envelope 21 is made from a film of the same thickness of the same plastic as the main envelope 6. However, in some applications it may be advantageous make the additional envelope 21 from a film of a different thickness of the same plastic, or the same or a different thickness of a different plastic.

The periphery 26 of the additional envelope 21 is attached to the surface of the main envelope 6. The additional envelope 21 has a segmented shape such that, when its periphery 26 is attached to the main envelope 6, and the additional chamber 31 formed between the outside of the main envelope 6 and the inside of the additional envelope 21 is inflated, the additional chamber 31 forms a cage structure inside or outside the main chamber 11, as shown in the figures. When the main envelope 6 is a polyhedral structure, the cage structure is preferably formed on the faces of the polyhedron. The parts of the main envelope 6 that do not form part of the wall of the additional chamber 31 provide a plurality of windows 46 that can be punctured to provide access for surgical instruments into and out of the main chamber 11.

The additional envelope 21 is attached, preferably to the outer surface of the main envelope 6, by welding along the periphery 26 of the additional envelope; alternatively, an adhesive may be applied to the periphery 26 of the additional envelope 21, and the additional envelope 21 brought into contact with the main envelope 6. Other methods that produce a flexible, gas-tight seal between the periphery 26 of the additional envelope 21 and the main envelope 6 may also be used.

One end of an additional inflation tube 41 is sealed into the additional envelope 21. The additional inflation tube 41 allows an inflation gas to pass into and out of the additional chamber 31. The inflation gas is typically air, nitrogen or carbon dioxide, although other suitable gases may be used. Typical inflation gas pressures are in the range 4 to 6 psi (2.8 to 4.1 kPa), the preferred pressure being 5 psi (3.5 kPa). The inflation gas pressure in the additional chamber is considerably higher than that in the main chamber to enable the additional chamber to exert sufficient force to keep already retracted organs in their retracted state despite the much smaller surface area of the additional chamber. The main inflation tube 16 is sealed through the additional envelope 21.

In an embodiment of the Type I retraction device designed for use in an insufflated body cavity, the main inflation tube 16 and the additional inflation tube 41 are contained within an inflation tube shield 61, which forms a gas-tight seal with the retraction device. The outer wall of the inflation tube shield 61 forms a gas-tight seal with the trocar or sheath through which it passes into the body cavity. The inflation tube shield 61 can be a separate component. Preferably, an extrusion can provide the inflation tube shield 61, the main inflation tube 16 and the additional inflation tube 41 in a unitary structure.

2. Type IA Retraction Device—Alternative Embodiments

The basic embodiment of a Type I retraction device has a single additional chamber 31. In alternative embodiments, additional chamber 31 is divided into a plurality of sub-chambers (not shown). The sub-chambers are isolated from one another, so that if one or more of them is accidentally punctured while the retraction device is in use, deflation of all of the retraction device can be avoided. Each sub-chamber can be equipped with its own additional inflation tube. Alternatively, each sub-chamber can be connected to an inflation manifold (not shown) through a non-return valve (not shown). This arrangement requires that each sub-chamber be deliberately punctured to deflate the retraction device in preparation for withdrawing the retraction device from the body at the end of the treatment procedure.

In a further alternative embodiment of the Type IA retraction device, the additional envelope 21 may be attached to the inner surface of the main envelope 6. In this embodiment, the main inflation tube 16 passes through the additional chamber and forms a gas-tight seal with the additional envelope 21 in addition to the main envelope 6.

In a further alternative embodiment of the Type IA retraction device, the additional envelope 21 need not be segmented. The additional chamber 31 is formed by attaching the additional envelope 21 to the main envelope 6, the line of attachment forming the periphery of the cage structure of the additional chamber 31. With this arrangement, each window 46 comprises a double thickness of film. This makes it somewhat more difficult to cut an aperture in a window.

Figure 24A:
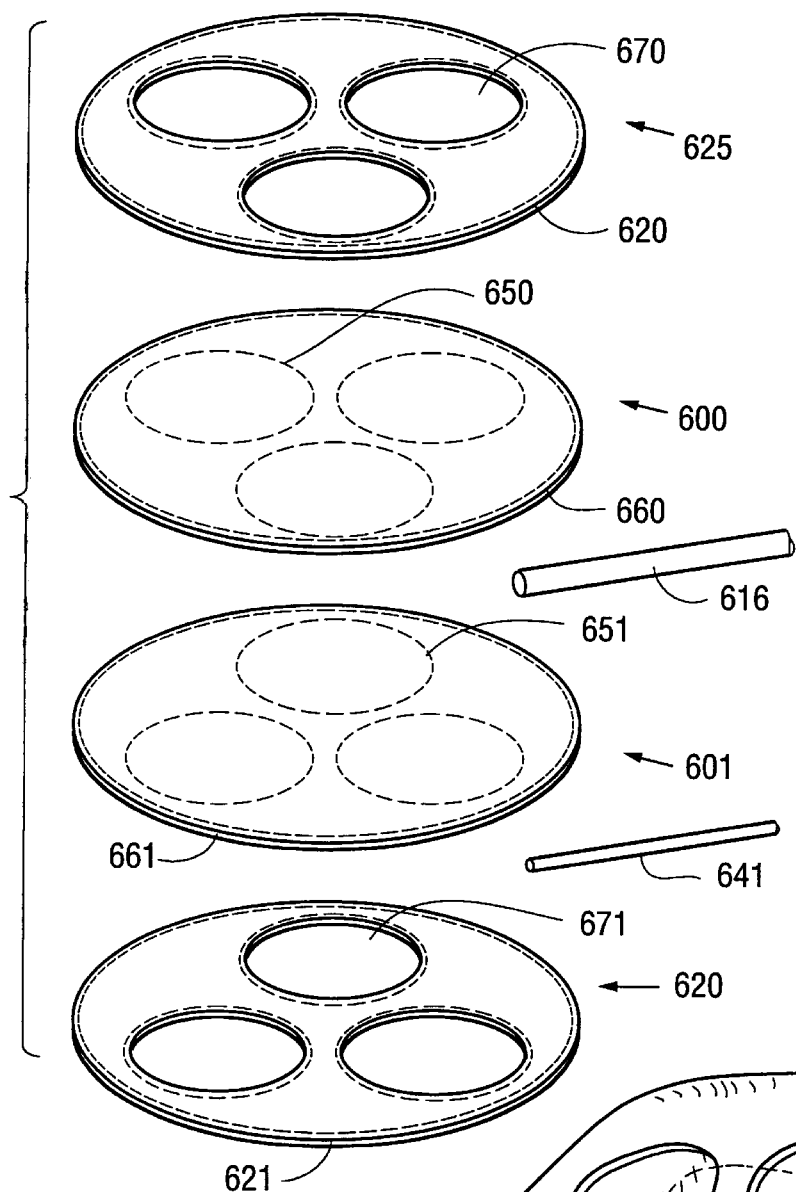
FIG. 24A is an exploded perspective view of the components of a flat Type IA retraction device illustrating the construction of such a device according to the invention.
Figure 24B:
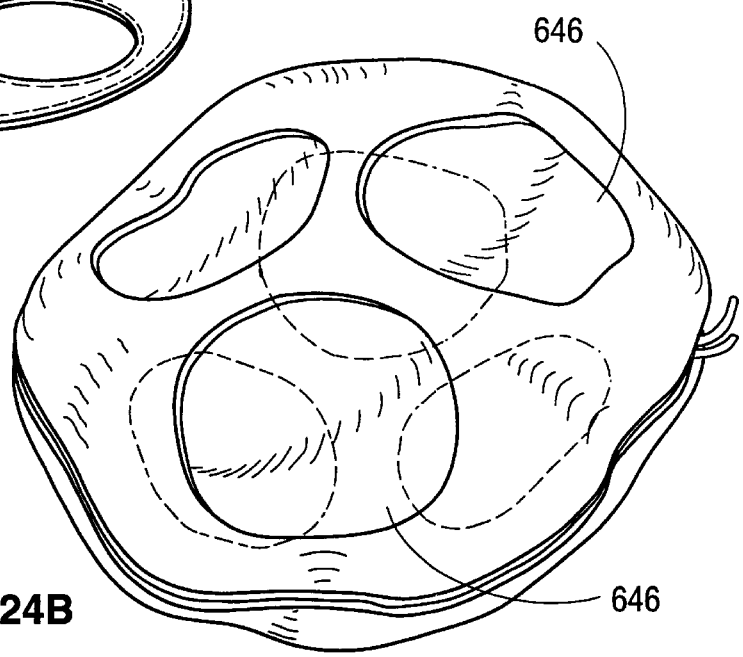
FIG. 24B is a perspective view of the assembled and inflated flat Type IA retraction device.

In a further alternative embodiment providing a relatively flat Type IA retraction device shown in FIG. 24B, neither the main envelope 6 nor the additional envelope 21 are segmented. The additional envelope 21 has a number of holes cut in it. The additional chamber 31 is formed by attaching the periphery of each hole in the additional envelope 21 to the main envelope 6.

Figure 25A:
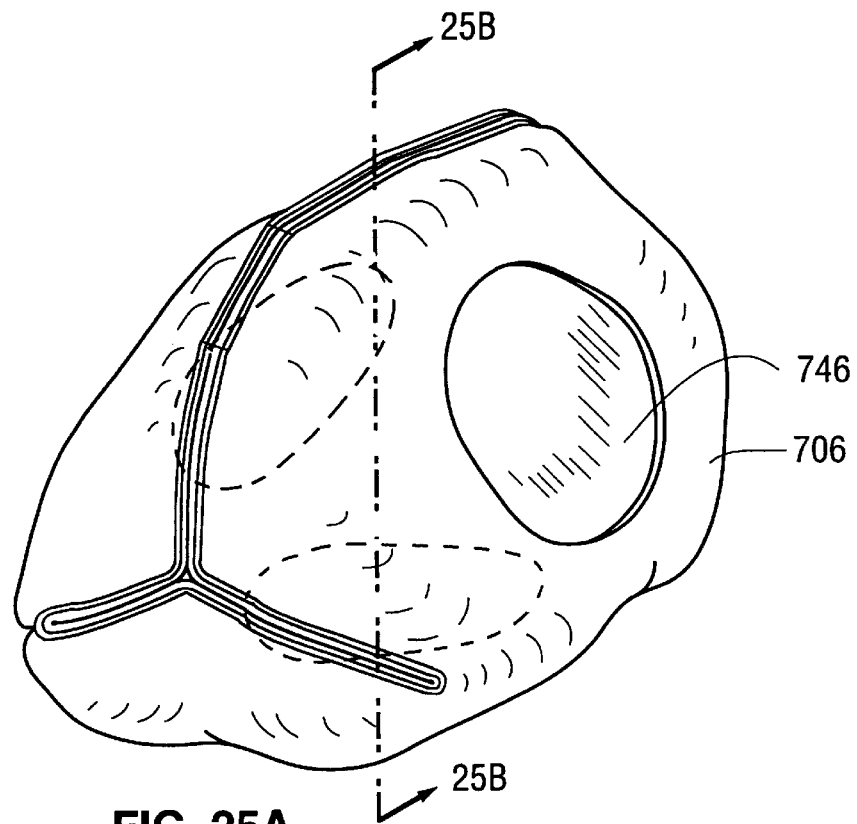
FIG. 25A is a perspective view of an inflated triangular prism-shaped Type IA retraction device according to the invention.
Figure 25B:
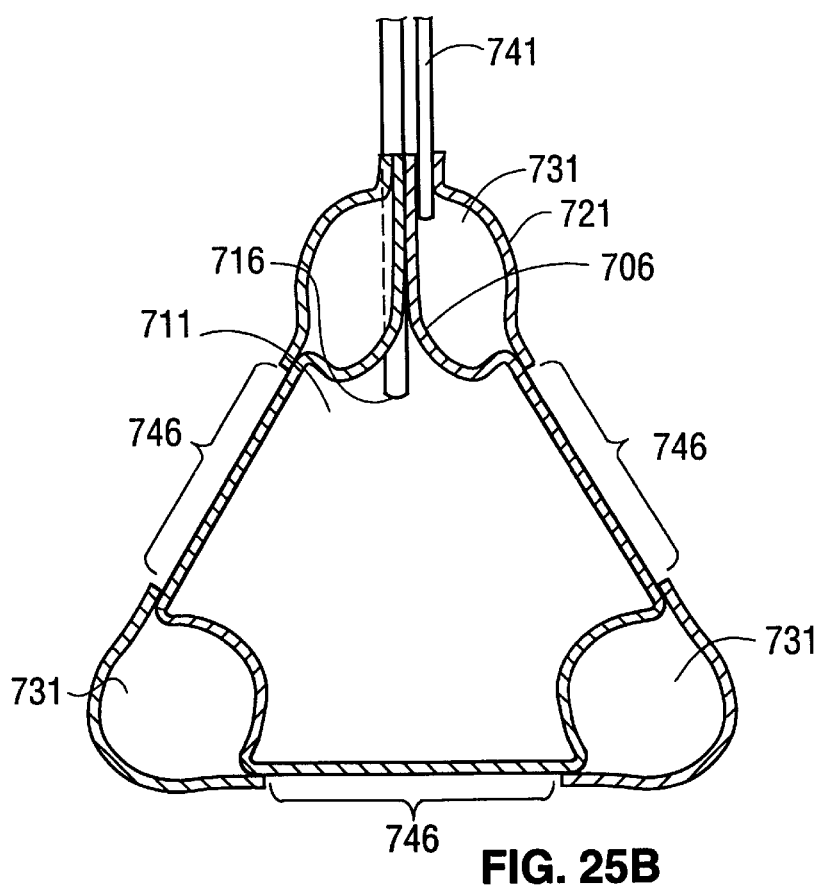
FIG. 25B is a vertical cross sectional view of an inflated the assembled triangular prism-shaped Type IA retraction device according to the invention along the line 25B—25B in FIG. 25A.
Figure 25C:
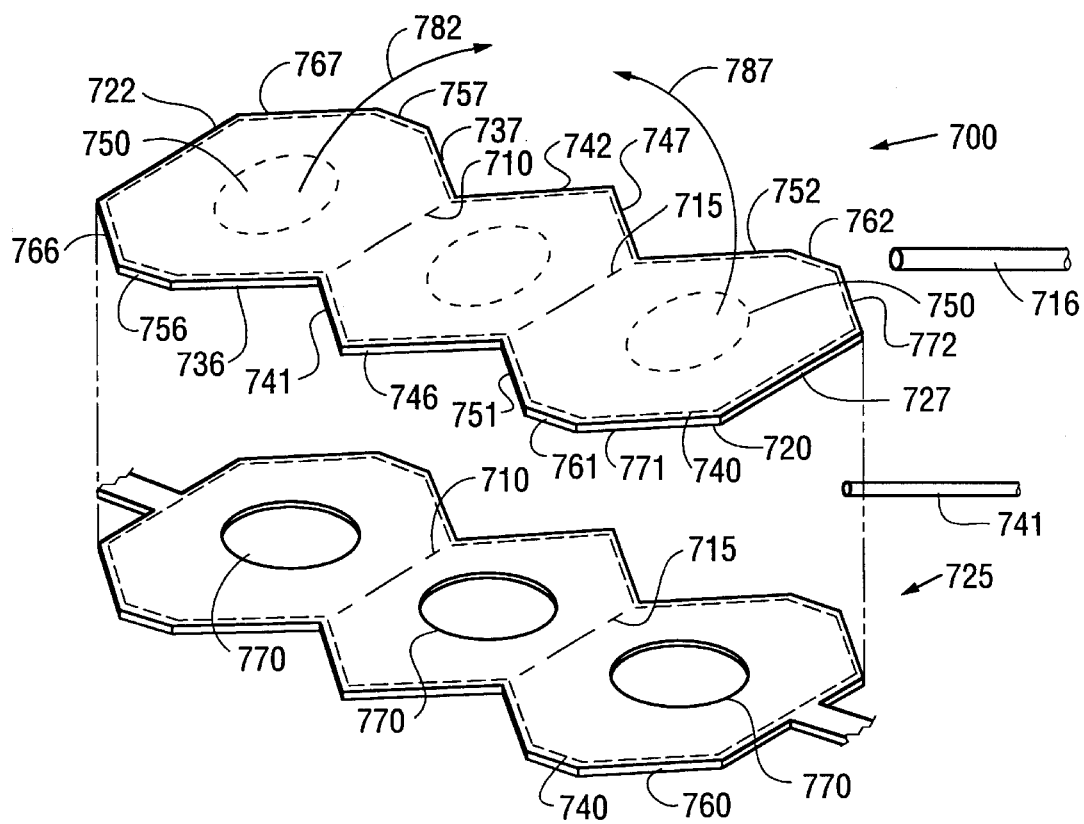
FIG. 25C is an exploded perspective view of the components of a triangular prism-shaped Type IA retraction device illustrating the construction of such a device according to the invention.
Figure 25D:
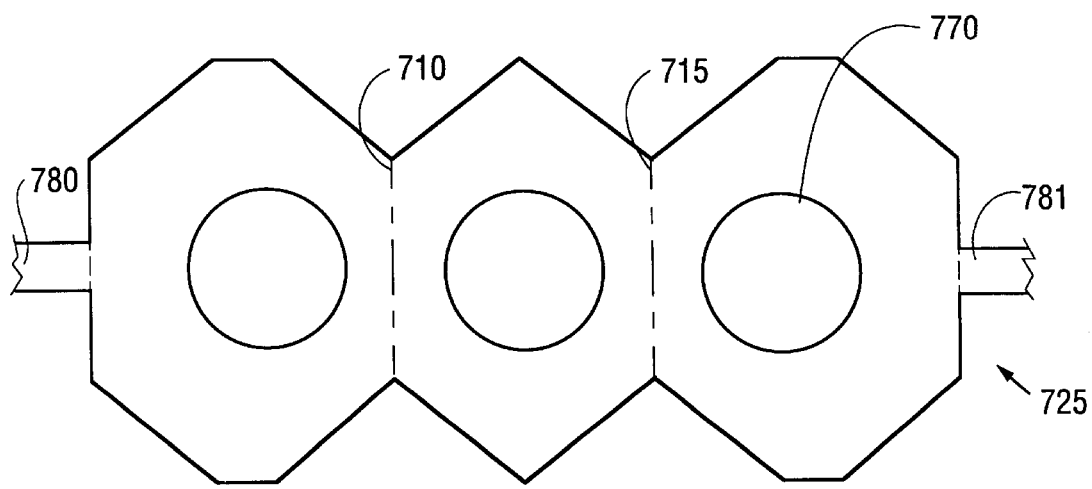
FIG. 25D is a plan view of the additional envelope blank of a triangular prism-shaped Type IA retraction device according to the invention.

In a further alternative embodiment, FIGS. 25A, 25B, 25C, and 25D show a Type IA retraction device in the shape of a triangular prism particularly suitable for use in the upper abdomen. In this embodiment, the main envelope 6 and the additional envelope 21 are serrated rectangles, as shown in FIGS. 25C and 25D. The additional envelope has three large holes cut in it. The additional chamber 31 is formed by attaching the periphery of each hole in the additional envelope 21 to the main envelope 6. Opposite ends of the long axis of the rectangle and the serrations are joined together to form the triangular structure.

All embodiments of the Type IA retraction device may be provided with tabs 56 on the inside the main envelope in accordance with a further aspect of the invention, as shown in FIGS. 2 and 3. The tabs 56 may be separate components attached to the inside of the main envelope 6 by welding, an adhesive, or some other suitable method. Alternatively, the tabs 56 can be an integral part of the main envelope 6 suitably extended into the main chamber 11. Tabs 56 provide points inside the main chamber 11 that can be gripped by a suitable gripping tool (not shown) inserted into main chamber 11 through the main inflation tube 16. The gripping tool allows the inflated retraction device to be manipulated to change its position so that, for instance, one of its windows can be aligned with the organ or tissue to be treated or observed. Partially deflating the inflated retraction device makes repositioning easier.

3. Type IA Retraction Device—Basic Method of Use

In the following description, the word "organ" will be used to mean an organ or a tissue that is retracted by the retraction device. The word "treat" will be used to mean both treat and observe, and the word "treatment" will be used to mean both treatment and observation. The word "tissue" or the phrase "tissue to be treated" will both be used to mean the organ or the tissue that is treated through or inside the retraction device.

FIGS. 4A through 4D show a cross sectional elevational view of the abdomen A to illustrate the method by which a Type IA retraction device according to the invention is inserted into the body and used to retract an organ within the body to gain access to treat a tissue. In the method illustrated in FIGS. 4A through 4D, the retraction device is inserted into the abdomen A and is used to retract an organ, the bowel B, to gain access to treat a tissue, the gall bladder GB. Similar methods are used to insert a retraction device according to the invention into other parts of the body.

Figure 4A:
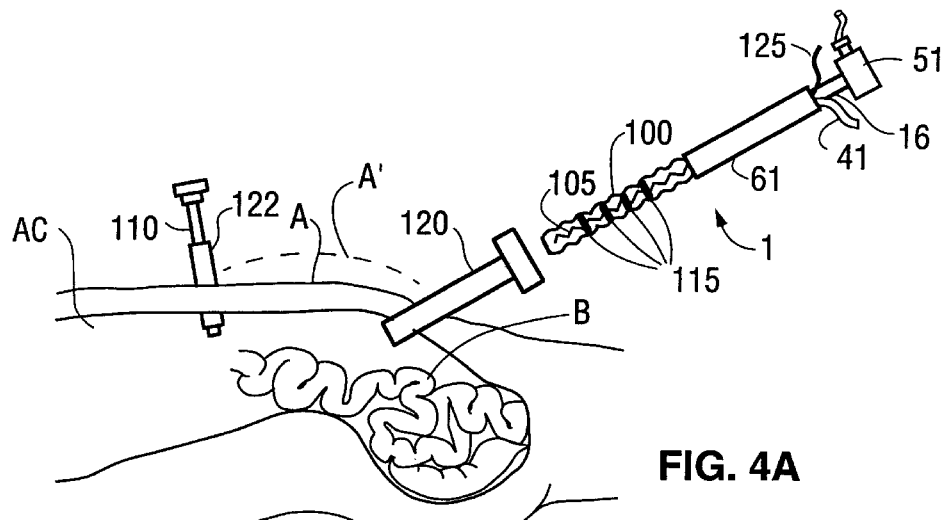
FIG. 4A is a longitudinal cross sectional elevational view of a body showing a packaged collapsed Type IA retraction device according to a first embodiment of the invention ready for insertion into the abdominal cavity.

Inflatable retraction device 1 is supplied in a collapsed state, as shown in FIG. 4A, in which it is tightly packaged in a configuration that makes it essentially a linear extension of the inflation tube shield 61. The retraction device 1 is packed so that when pressure is applied to the main inflation tube 16, the retraction device 1 deploys without tangling. Depending on the size of the retraction device 1, the packaged retraction device will fit through an insertion tube (usually a trocar tube) of between 3 and 20 mm (0.12"–0.8") in diameter, a typical diameter being 14 mm (0.55"). The retraction device 1 is retained in its collapsed state by the sleeve 100 which, in turn, is held together by one-pull lacing 105. Alternatively, the sleeve 100 can be fitted with a tear-off strip (not shown). Pulling on the thread 125 detaches the one-pull lacing 105 or the tear-off strip from the sleeve 100, releasing the collapsed retraction device 1.

The sleeve 100 can be provided with suitable markings 115 to enable its orientation to be determined and, if necessary, adjusted, after insertion into the body and before inflation.

Prior to starting the procedure, the abdomen A may be lifted to provide additional working space by gas insufflation, or by one of the mechanical devices disclosed in U.S. patent application Ser. No. 706,781, of which application this application is a Continuation-in-Part. The insufflated condition of the abdomen A is indicated by the broken line A'.

A small incision is made in the skin of the abdomen A and a trocar (not shown) and trocar tube 120 are inserted into the incision and are driven through the wall of the abdomen A. The trocar is withdrawn. A second small incision is made in the skin of the abdomen A and a trocar (not shown) and trocar tube 122 are inserted into the incision and driven through the wall of the abdomen. The trocar is withdrawn and an endoscope 110 is inserted into the trocar tube 122. The second incision is located so that the endoscope 110 can observe the intended placement site of the retraction device 1. Alternatively, a small endoscope (not shown), preferably about 2 mm (0.1") in diameter, may be attached to the collapsed retraction device so that the location of the retraction device inside the abdomen may be determined. With this approach, the endoscope 110 is not used, and the second incision need not be made.

Figure 4B:
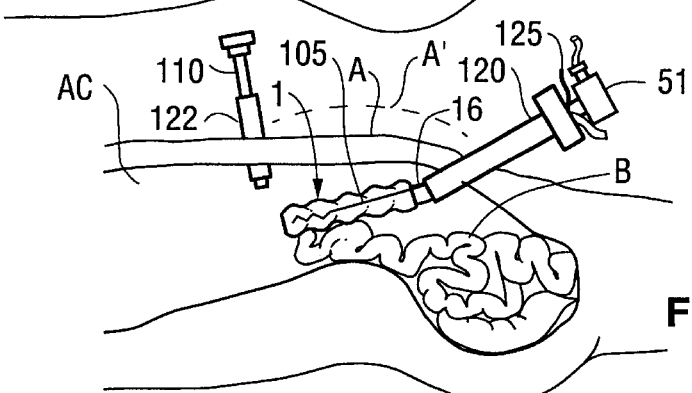
FIG. 4B is a longitudinal cross sectional elevational view of a body showing a packaged collapsed Type IA retraction device according to a first embodiment of the invention after it has been inserted into the abdominal cavity.

The collapsed retraction device 1 is threaded, with the aid of its inflation tube shield 61, through the trocar tube 120 into the abdominal cavity AC, as shown in FIG. 4B, and manipulated into its correct position. The position of collapsed retraction device 1 in the abdominal cavity AC is observed through the endoscope 110: the markings 115 enable the orientation of retraction device 1 to be determined and adjusted if necessary. Alternatively, the position of the collapsed retraction device is determined by means of the small endoscope (not shown) attached to the retraction device.

The thread 125 is then pulled to release the sleeve 100 from around collapsed retraction device 1, and the sleeve 101 is withdrawn from the abdominal cavity AC through the trocar tube 120 by means of the thread 125.

Figure 4C:
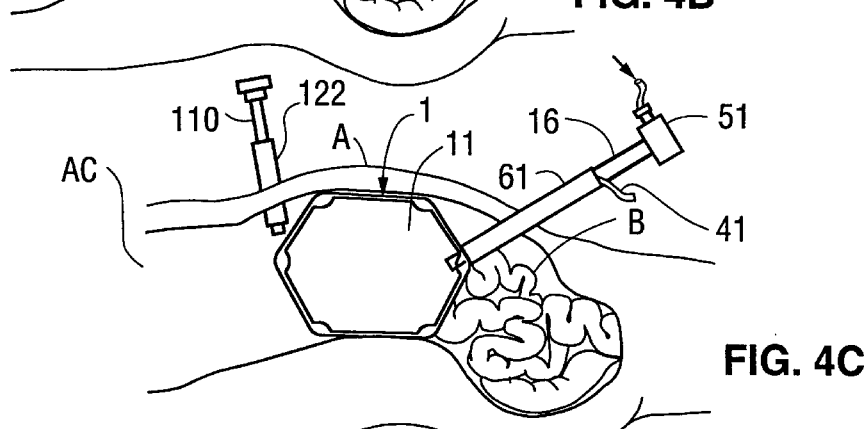
FIG. 4C is a longitudinal cross sectional elevational view of a body showing a Type IA retraction device according to a first embodiment of the invention during the inflation of its main chamber in the abdominal cavity.

Once the retraction device 1 is correctly positioned, and released from its sleeve 100, the main inflation tube 16 is connected to a source of inflation gas (not shown) and the gas supply is slowly turned on to inflate the main chamber 11. The retraction device 1 slowly expands, as shown in FIG. 4C, progressively displacing the bowel B as its size increases. Throughout the expansion process, the retraction device 1 presents a relatively large surface area to the bowel B, and thus displaces the bowel B gently, progressively, and without trauma. Although the retraction device 1 retracts the bowel B gently, the main chamber of the retraction device is capable of exerting the force necessary to effect the displacement the bowel B.

Once the retraction device 1 has reached its fully-inflated condition, its position is checked by viewing it through the endoscope 110 and/or an endoscope 110 (FIG. 4E) inserted into its main chamber 11 via the main inflation tube 16 and the port 51. Alternatively, an endoscope 110a (FIG. 4E) may be inserted into the main chamber 11 via the main inflation tube 16 prior to or during inflation, so that observation may be-made through the balloon before, during, and/or after inflation of the balloon. The port 51 prevents loss of inflation pressure of the main chamber 11 when the endoscope extends through the port. The ability to observe (through the balloon) the area surrounding the balloon assists the user in positioning of the balloon and also provides visualization of the work area located outside the balloon as the surgical procedure is being performed. The tissue to be treated must be covered by one of the windows 46 of retraction device 1.

If the retraction device 1 is not correctly positioned, the inflation gas pressure is reduced slightly to partially deflate retraction device 1. A suitable gripping tool is passed through the port 51 and the main inflation tube 16 into the interior of the retraction device 1, to grip one of the tabs 56 (FIGS. 2 and 3). The gripping tool is manipulated to correct the positioning error while the position of the retraction device 1 is observed through the endoscope 110 or the endoscope 110a (FIG. 4E) in the main chamber 11. Once the error is corrected, the main chamber 11 of the retraction device 1 is reinflated by means of the main inflation tube 16.

Figure 4D:
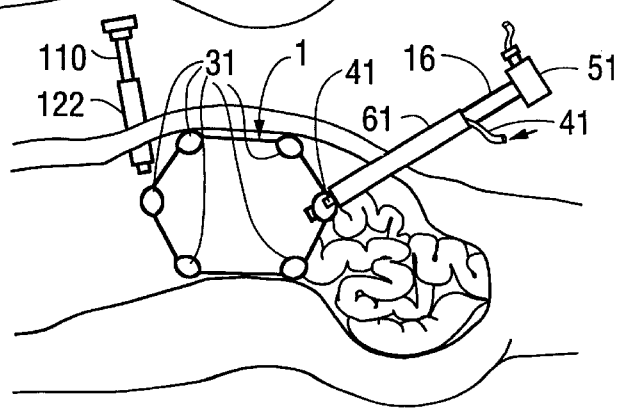
FIG. 4D is a longitudinal cross sectional elevational view of a body showing a Type IA retraction device according to a first embodiment of the invention after the additional chamber has been inflated and the inflation pressure has been removed from the main chamber in the abdominal cavity.
Figure 4E:
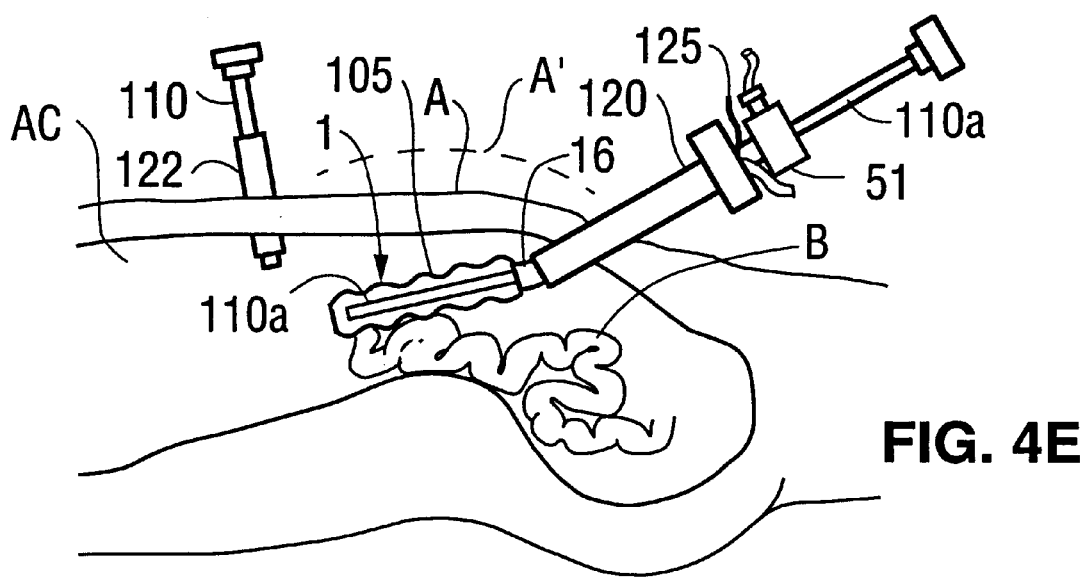
FIG. 4E is a longitudinal cross sectional elevational view of a body showing a packaged collapsed Type IA retraction device according to a first embodiment after it has been inserted into the abdominal cavity and after insertion of an endoscope into the balloon chamber.

Once the retraction device 1 is correctly positioned, the additional inflation tube 41 is connected to a source of inflation gas (not shown) and the additional chamber 31 is inflated to the required pressure, as shown in FIG. 4D. After the additional chamber 31 is fully inflated, the source of inflation pressure can be removed from the main chamber 11 and the main inflation tube 16. The port 51 can be removed from the main inflation tube 16 since a gas-tight seal is no longer required around instruments inserted into the main inflation tube 16, the main chamber 11 now being at atmospheric pressure.

Figure 5:
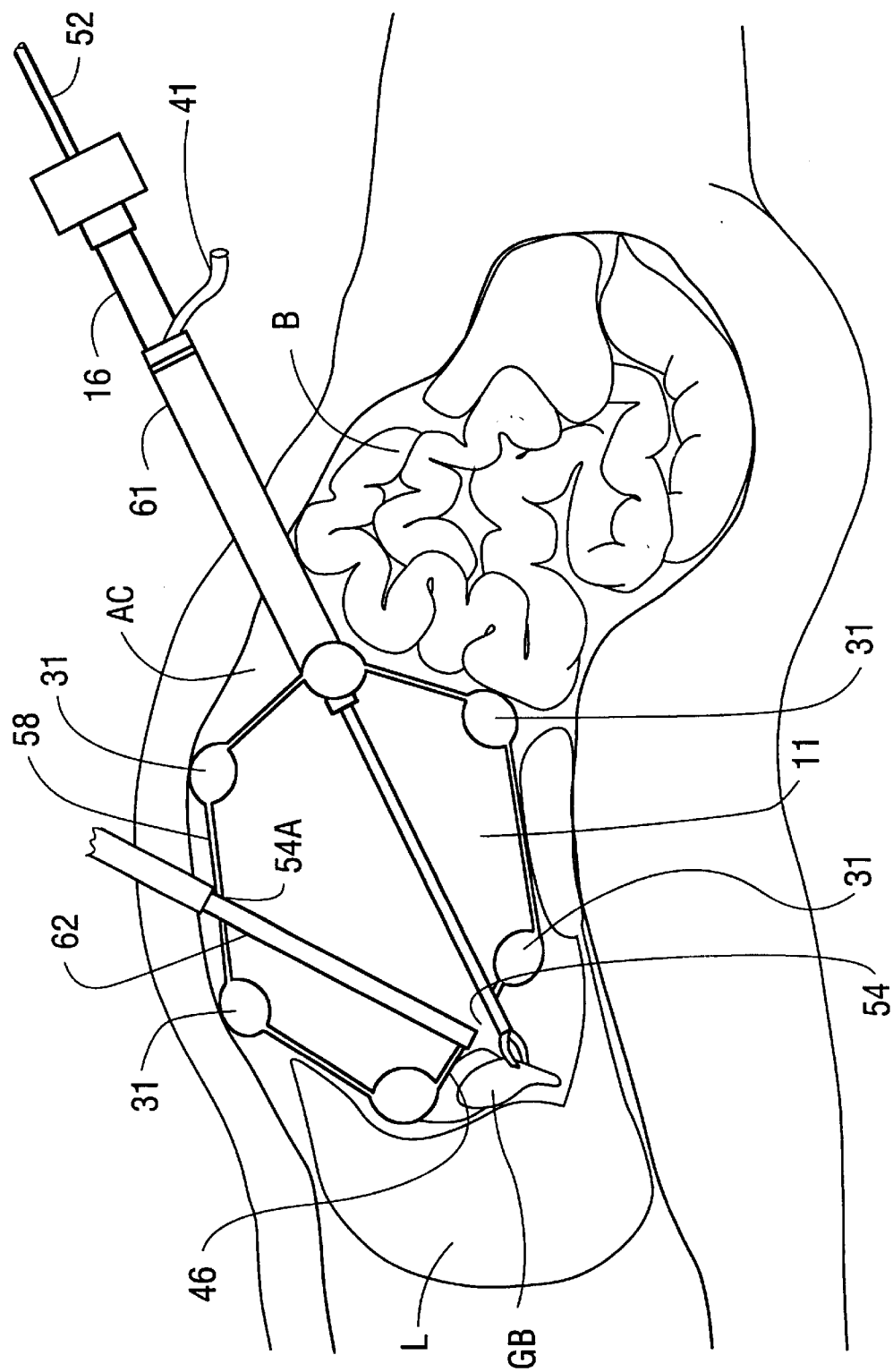
FIG. 5 is a longitudinal cross sectional elevational view of a body showing a Type IA retraction device according to a first embodiment of the invention used to retract the bowel and lift the liver to expose the gall bladder for observation by an endoscope inserted into the main chamber of the retraction device through the main inflation tube.

A cutting instrument 52 is then passed through the main inflation tube 16 into the main chamber 11 to cut a suitable aperture 54 in the window 46 that covers of the tissue to be treated, as shown in FIG. 5. Alternatively, an additional puncture may be made in the abdominal wall and a cutting instrument 62 passed through this puncture to cut an aperture 54A in a window 58 to gain access to the main cavity 11, and thence to cut a suitable aperture 54 in the window 46. The aperture 54 provides an access to the tissue to be treated; for example, the gall bladder GB. The aperture 54 may simply be a cut in the window 46, or all or part of the window 46 may be removed to provide the aperture 54. Those procedures that are carried out using instruments passed through the aperture 54 in the window 46 require that more of the window 46 be removed than those procedures in which the tissue to be treated is pulled inside the retraction device. When the tissue to be treated is treated inside the retraction device, the periphery of the aperture 54 through which the tissue is pulled may form a seal around the tissue and isolate it from the body outside the retraction device.

If the main inflation tube is not conveniently placed relative to the tissue to be treated, or if more surgical instruments than can be accommodated by the main inflation tube 16 are needed to perform the treatment, an alternative way of passing instruments into the main chamber 11 is to make at least one further incision in the body wall, the further incision being made in a location adjacent a further window 58 of the retraction device, as shown in FIG. 5. A trocar (not shown) with tube 60 is inserted into the further incision and is driven through the body wall to pierce the further window 58. The trocar is withdrawn leaving the trocar tube 60 in place. Instruments, e.g., instrument 62 are then inserted into the retraction device as required through the trocar tube 60 and the further window 58.

FIG. 5 additionally shows the retraction device 1 in place in the abdominal cavity AC in its fully inflated form. The main chamber 11 is not pressurized; the shape of the retraction device is maintained by the inflated additional chamber 31. In FIG. 5, retraction device 1 was placed before inflation such that when the main chamber 11 was inflated, the expansion of the retraction device 1 displaced the bowel B to the right of the drawing and lifted the liver L upwards to expose the tissue to be treated, i.e., the gall bladder GB.

After the treatment is completed, the additional chamber 31 is disconnected from the source of inflation pressure and the pressure in the additional chamber 31 is released to collapse the retraction device. Collapsing the retraction device is assisted by connecting the additional inflation tube 41 to a vacuum line (not shown) to evacuate the additional chamber 31. Once the retraction device 1 is fully collapsed, the trocar tube 120 is withdrawn from the abdominal cavity, the retraction device 1 is withdrawn through the small abdominal opening, and the openings in the abdominal wall are closed in the normal way.

4. Type II Retraction Device—Basic Embodiment

FIG. 6 shows an alternative embodiment 201 of a retraction device that maintains its shape while allowing treatment to be carried out working through or inside it. The alternative embodiment lacks the second inflatable chamber of the Type I embodiment shown in FIGS. 1 through 5, and has only a main envelope 206 enclosing a main chamber 211. The single chamber embodiment of the retraction device will be designated as a Type II retraction device. The main chamber 211 remains inflated throughout the treatment process, access to the tissue to be treated being provided by an elastomeric window 261 attached to the main envelope 206. The elastomeric window 261 is self-sealing and maintains inflation pressure in the main chamber 211 by forming a substantially gas-tight seal around instruments passed through it. The elastomeric window 261 also forms a substantially gas-tight seal around the tissue to be treated if the tissue to be treated is pulled through the elastomeric window 261 into the main chamber 211 for treatment.

The main envelope 206 is made of a relatively inelastic and tough film of a plastic such as Mylar®, polyethylene, or polyurethane. The preferred material for the main envelope is a polyethylene and nylon composite. The thickness of the main envelope 206 is typically from 0.5 to 5 mils (13 to 130 microns). The proximal end of a main inflation tube 216 is sealed into the main envelope 206. The main inflation tube 216 allows an inflation gas to pass into and out of the main chamber 211. The inflation gas is typically air, nitrogen or carbon dioxide, although other suitable gases may be used. Typical inflation gas pressures are in the range 0.3 to 0.7 psi (0.21 to 0.48 Pa), the preferred pressure being 0.5 psi (0.35 kPa). Once the main chamber 211 is fully inflated, the inflation gas pressure can be reduced to about 0.3 psi (0.21 kPa). The main inflation tube 216 is provided with a port 251 on its distal end, through which endoscopes and other surgical instruments can be passed into the main chamber 211. The port 251 provides a gas-tight seal around instruments passed through it and allows inflation pressure to be maintained in the main chamber 211 with instruments present.

The main envelope 206 of the Type II retraction device shown in FIG. 6 is a polyhedral structure constructed from two segmented, substantially flat pieces of plastic film, which gives the retraction device a substantially polyhedral shape. Alternatively, two non-segmented substantially flat pieces of plastic film can be used to make a relatively flat Type II retraction device. In a further alternative, the retraction device can be constructed from curved pieces of plastic film, which gives the retraction device a substantially spherical or spheroidal shape.

The size of Type II retraction devices according to the invention can range from about 2" (50 mm) wide by about 0.5" (12 mm) high, for instance for use inside the pericardium, to 10"–14" (250–350 mm) wide by 4"–8" (100–200 mm) high, for use in the abdominal cavity. The size of retraction device required for a given application depends on the application and the size of the patient.

The lack of a additional chamber in the retraction device 201 shown in FIG. 6 makes orientation less critical. If the main envelope 206 is constructed from one or two curved pieces of film, orientation is particularly uncritical. If the main envelope 206 is a polyhedral structure having a number of faces, some orientation is required because the tissue to be treated must be substantially centered on one of the faces. The retraction device 201 can be provided with tabs 256 on the inside the main envelope 206. Tabs 256 may be separate components attached to the inside of the main envelope 206 by welding, an adhesive, or some other suitable method. Alternatively, tabs 256 can be an integral part of the main envelope 206 suitably extended into the main chamber 211. Tabs 256 provide points on the inside of the main chamber 211 that can be gripped by a suitable gripping tool (not shown) inserted into main chamber 211 through the inflation tube 216 and port 251. The gripping tool allows the inflated retraction device 201 to be manipulated to change its position so that the desired point on the tissue to be treated can be substantially centered on one of its faces. Partially deflating the inflated retraction device makes repositioning easier.

The elastomeric window 261 is installed on the inside of the main envelope 206 after the retraction device 201 has been placed in the body and inflated. The elastomeric window 261 is shown in FIG. 7 and comprises a flat piece 266 of a film of an elastomeric material such as latex or silicone rubber about 0.5" to 1.5" (12 to 37 mm) in diameter. The periphery of the elastomeric film 266 is attached by means of a suitable adhesive, such as an acrylic cement or a silicone adhesive to one of the flat faces of a ring 271 having a square or rectangular cross section. The ring 271 is circular or elliptical in shape and is of a springy material such as polyethylene or stainless steel, so that will regain its circular or elliptical shape after being compressed across one of its diameters to enable it to be passed through the inflation tube 216. The other flat face 276 of the ring 271 is coated with an adhesive. A pressure-sensitive adhesive such as a contact rubber adhesive may be used. In the preferred embodiment a hot-melt adhesive of the type used in woodworking glue guns is used. If a hot-melt adhesive is used, a heating element 281, made of a suitable resistance wire, such as Nichrome, is inserted into a narrow groove in the face 276 of the ring 271 to which the adhesive is applied. Suitable electrical leads 291 are connected to the heating element 281.

Before it can be inserted into the retraction device 201, the elastomeric window must be wrapped across one of its diameters to reduce its width so that it can pass through the main inflation tube 216, as shown in FIG. 8. A one-pull lacing arrangement 205, or a sleeve with a tear strip (not shown) can be used. Wrapped elastomeric window 261 is attached to a manipulation rod 286 for insertion into the retraction device. Also attached to the manipulation rod is the thread 225 to release the one-pull lacing 205 or the tear strip (not shown) and, if a temperature-sensitive adhesive is used, the electrical leads 291 for the heating element 281 (FIG. 7).

The wrapped elastomeric window 261 on the end of the manipulating rod 286 is passed through the port 251 and the main inflation tube 216 into the main chamber 211. The lacing 205 or tear-strip is released, which allows the elastomeric window 261 to resume its circular shape. The elastomeric window 261 is then manipulated to bring it into contact with the main envelope 206 such that the elastomeric window 261 covers the tissue to be treated. If a pressure-sensitive adhesive is used, the face 276 of the elastomeric window is pushed against the main envelope 206 to affix the elastomeric window 261 in place. If a hot-melt adhesive is used, the face 276 of the elastomeric window is placed against the main envelope 206 and a suitable source of electric current (not shown) is applied to the electrical leads 291 for the time required to melt the adhesive and affix the elastomeric window 261 to the main envelope 206.

Once the elastomeric window 261 is firmly affixed to the main envelope 206, the manipulating rod 286 is detached from it and withdrawn from the main chamber 211. A suitable cutting instrument 252 is passed through the port 251 and the main inflation tube 216 into the main chamber 211 and through the elastomeric window 261, as shown in FIG. 6. The elastomeric window 261 forms a gas-tight seal around the cutting instrument 252, and re-seals itself after the cutting instrument 252 is withdrawn. The cutting instrument 252 is used to cut an aperture in the part 296 of the main envelope 206 that is covered by the elastomeric window 261. The part 296 of the main envelope 206 is shown by shading in FIG. 9. The aperture 254 may simply be a cut in the part 296 of the envelope 206, or all or part of the part 296 of the envelope 206 may be removed to provide the aperture 254. Procedures that are carried out using instruments passed through the elastomeric window 261 require removing more of the part 296 of the envelope 206 than procedures in which the tissue to be treated enters the retraction device through the aperture 254 and the elastomeric window 261. When the tissue to be treated is treated inside the retraction device 201, the elastomeric window 261 forms a seal around the tissue and isolates it from the body outside the retraction device. The treatment procedure is then carried out by inserting instruments through the port 251 and the main inflation tube 216 into the main chamber 211 and either working through the elastomeric window 261 or working on the tissue to be treated inside the cavity 211.

5. Type II Retraction Device—Basic Method of Use

Figure 10A:
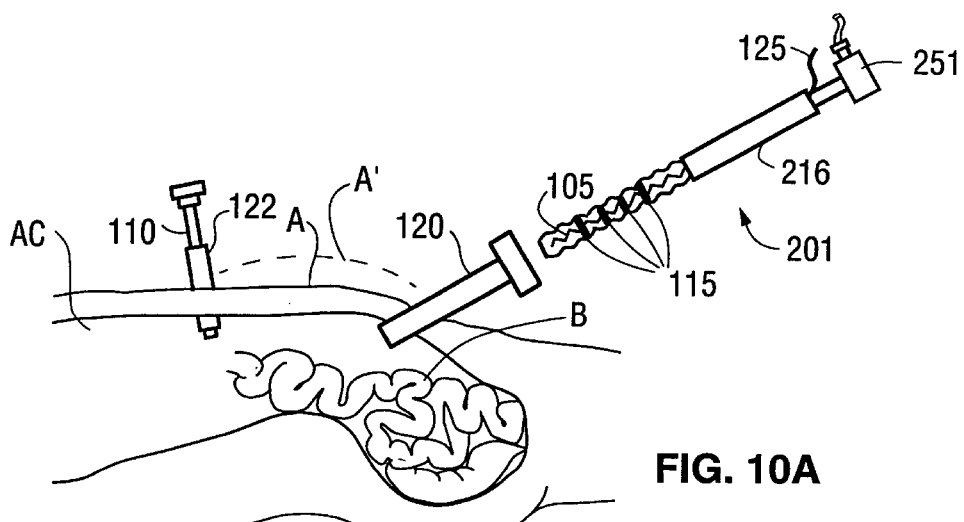
FIG. 10A is a longitudinal cross sectional elevational view of a body showing a packaged collapsed Type II retraction device according to a second embodiment of the invention ready for insertion into the abdominal cavity.

The retraction device 201 is inserted into the abdomen using a procedure similar to that used to insert a Type IA retraction device. Inflatable retraction device 201 is supplied in a collapsed state, as shown in FIG. 10A, in which it is tightly packaged in a configuration that makes it essentially a linear extension of the main inflation tube 216. The retraction device 201 is packed so that when inflation pressure is applied to the main inflation tube 216, retraction device 201 deploys without tangling. Depending on the size of the retraction device 201, the packaged retraction device will fit through an insertion tube of between 3 and 20 mm (0.12"–0.8") in diameter, a typical diameter being 14 mm (0.55"). The retraction device 201 is retained in its collapsed state by a sleeve 100 which, in turn, is held together by one-pull lacing 105 or a tear strip (not shown).

The sleeve 100 can be provided with suitable markings 115 to enable its orientation to be determined and, if necessary, adjusted, after insertion into the abdomen and before inflation.

Prior to inserting the retraction device, the abdomen A may be lifted to provide additional working space by gas insufflation, or by one of the mechanical devices disclosed in U.S. patent application Ser. No. 706,781, of which application this application is a Continuation-in-Part. The insufflated state of the abdomen A is indicated by the broken line A'.

A small incision is made in the skin of the abdomen A and a trocar (not shown) and trocar tube 120 are inserted into the incision and are driven through the wall of the abdomen A. The trocar is withdrawn. A second small incision is made in the skin of the abdomen A and a trocar (not shown) and trocar tube 122 are inserted into the incision and driven through the wall of the abdomen. The trocar is withdrawn and an endoscope 110 is inserted into the trocar tube 122. The second incision is located so that the endoscope 110 can observe the intended placement site of the retraction device 1. Alternatively, a small endoscope (not shown), preferably about 2 mm (0.14") in diameter, may be attached to the collapsed retraction device so that the location of the retraction device inside the abdomen may be determined. With this approach, the endoscope 110 is not used, and the second incision need not be made.

The collapsed retraction device 201 is threaded, with the aid of its main inflation tube 216, through the trocar tube 120 into the abdomen A, and manipulated into its correct position. The position of collapsed retraction device 201 is observed through the endoscope 110: the markings 115 enable the orientation of the retraction device to be determined and adjusted if necessary. Alternatively, the position of the collapsed retraction device is determined by means of the small endoscope (not shown) attached to the retraction device.

Figure 10B:
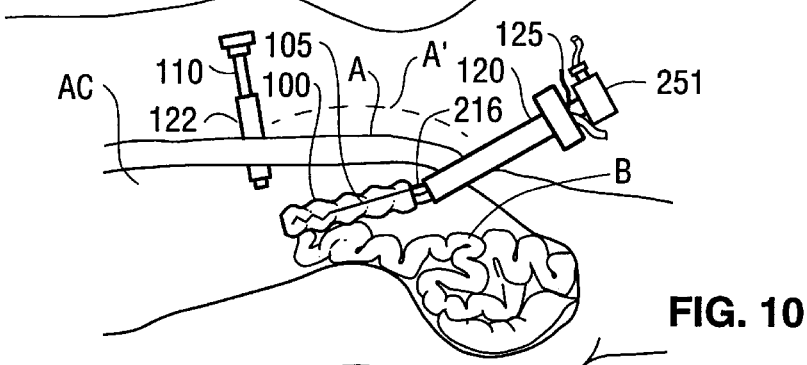
FIG. 10B is a longitudinal cross sectional elevational view of a body showing a packaged collapsed Type II retraction device according to a second embodiment of the invention after it has been inserted into the abdominal cavity.
Figure 10C:
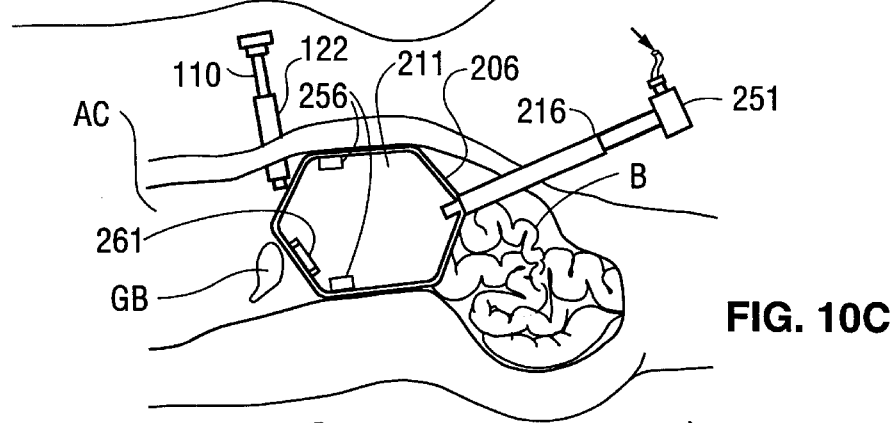
FIG. 10C is a longitudinal cross sectional elevational view of a body showing a Type II retraction device according to a second embodiment of the invention during the inflation of its main chamber in the abdominal cavity.

The thread 125 is then pulled to release the sleeve 100 from around the collapsed retraction device 201, as shown in FIG. 10B, and the sleeve 100 is withdrawn from the abdominal cavity AC through the trocar tube 120 by means of the thread 125. The main inflation tube 216 is connected to a source of inflation gas (not shown). The inflation gas pressure is slowly increased to inflate the main chamber 211. The retraction device 201 slowly expands, progressively displacing the bowel B as its size increases, as shown in FIG. 10C. Throughout the expansion process, the retraction device 201 presents a relatively large surface area to the bowel B, and thus displaces the bowel gently, progressively, and without trauma. Although the retraction device 201 retracts the bowel B gently, the main chamber of the retraction device 201 is capable of exerting the force necessary to effect the displacement of the bowel.

Figure 10D:
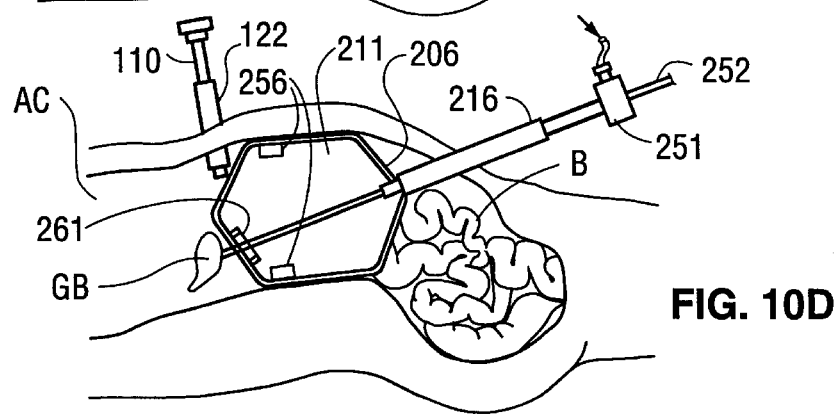
FIG. 10D is a longitudinal cross sectional elevational view of a body showing a Type II retraction device according to a second embodiment of the invention in its fully inflated condition in the abdominal cavity.

Once retraction device 201 has reached its fully-inflated condition, its position is checked by viewing it through either the endoscope 110 and/or an endoscope (not shown) inserted into the main chamber 211 of the retraction device 201 via the port 251 and the main inflation tube 216. The tissue to be treated should be in contact with the main envelope 206 and lie substantially directly in line with the main inflation tube 216. Further, if the retraction device is a polyhedron, the tissue to be treated should be substantially centered in one of its faces. The position of the retraction device 201 can be adjusted by gripping one or more of the tabs 256 with a suitable gripping tool (not shown), as described above. Once the retraction device 201 is correctly positioned, the elastomeric window 261 may be installed as described above. FIG. 10D shows the retraction device 201 in its fully inflated state with the elastomeric window 261 installed, and the instrument 252 passed through the elastomeric window 261 and the aperture 254 in the main envelope 206 to treat the tissue to be treated, the gall bladder, GB.

After the treatment is completed, the main chamber 211 is disconnected from the source of inflation pressure and the pressure in the main chamber 211 is released to collapse the retraction device. Collapsing the retraction device is assisted by connecting the main inflation tube 216 to a vacuum line (not shown) to evacuate the main chamber 211. Once fully collapsed, the retraction device 201 is withdrawn from the abdominal cavity through the opening in the abdominal wall that remains after withdrawing the trocar tube 120. The elastomeric window 261 is sufficiently flexible to be withdrawn through the opening in the abdominal wall along with the retraction device 201. The openings in the abdominal wall are then closed in the normal way.

6. Type IB Retraction Device

Figure 11A:
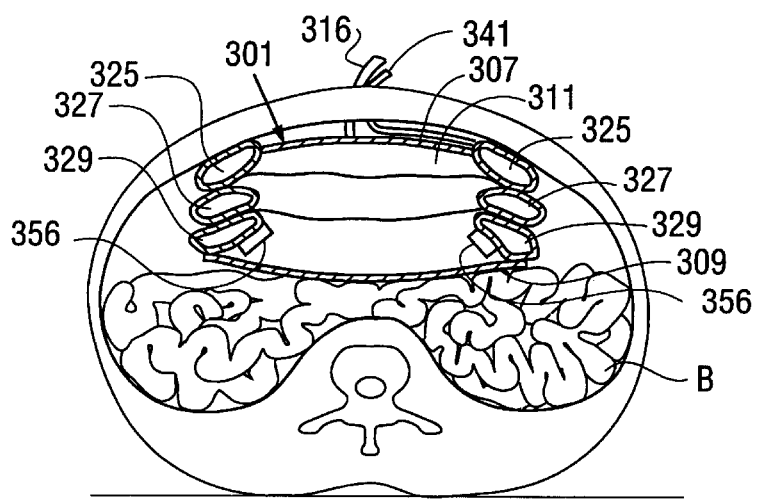
FIG. 11A is a transverse cross sectional elevational view of the abdomen showing a Type IB retraction device according to a third embodiment of the invention during the inflation of its main chamber in the abdominal cavity.
Figure 11B:
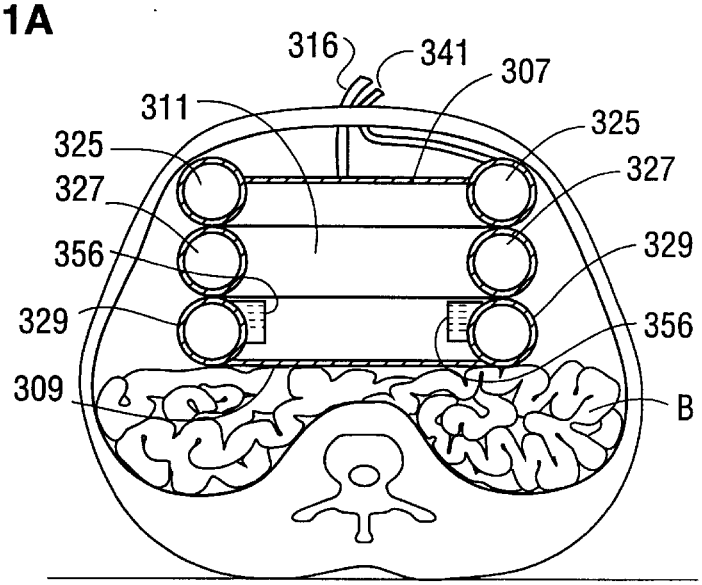
FIG. 11B is a transverse cross sectional elevational view of the abdomen showing a Type IB retraction device according to a third embodiment of the invention in its fully inflated condition in the abdominal cavity.
Figure 11C:
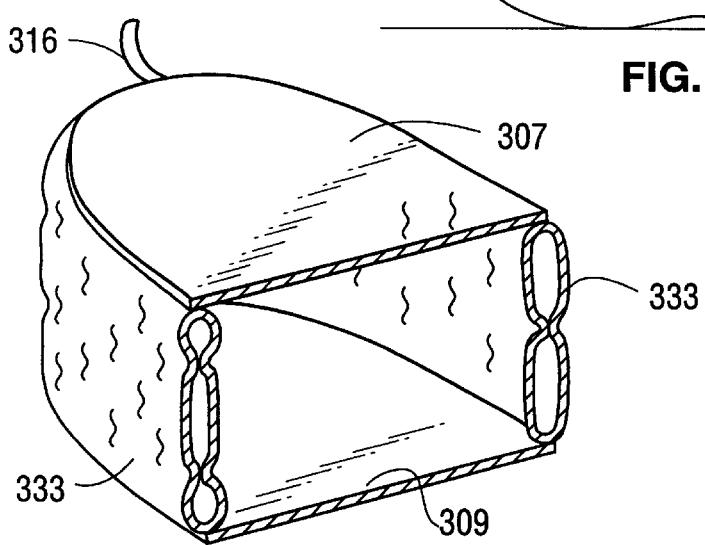
FIG. 11C is a perspective view of a Type IB retraction device according to a third embodiment of the invention showing an alternative form of additional cavity having tacked sidewalls.

A further embodiment of the invention, which is a variation on the Type I retraction device, designated Type IB, is shown in FIGS. 11A, 11B, and 11C. This variation has the advantage of providing two large, flat windows, but has the disadvantage that it does not allow any access to tissues lying to the side of the retraction device. The retraction device 301 shown in FIGS. 11A and 11B is substantially cylindrical in shape. A stack of one or more toroidal chambers forms the additional chamber 331. The example shown in FIGS. 11A and 11B has 3 toroidal chambers 325, 327 and 329. Alternatively, as shown in FIG. 11C, a single chamber having sidewalls 333 that are tacked together can be used for the additional chamber 331. In this alternative embodiment, the tacked sidewalls form an enclosure having a height that is considerably greater than its width. In FIGS. 11A, 11B, and 11C, the diaphragms 307 and 309 cover the top and bottom, respectively, of the retraction device 301. The diaphragms 307 and 309, together the inner walls of the toroidal chambers 325, 327, and 329, form the main chamber 311.

The main inflation tube 316 is sealed into the main chamber 311 and allows the main chamber to be inflated. The additional inflation tube 341 is sealed into the additional chamber 331. If more than one toroidal chamber is used to provide the additional chamber, the toroidal chambers may be interconnected and a single additional inflation tube 341 used, or each toroidal chamber may be provided with its own additional inflation tube (not shown). The latter approach prevents the retraction device 301 from collapsing completely if one of the toroidal chambers 325, 327, or 329 is accidentally punctured, and also allows the height of the retraction device to be adjusted by selectively inflating the toroidal chambers 325, 327, or 329.

The Type IB retraction device shown in FIGS. 12 and 13 is constructed from similar materials to the Type IA retraction device, and may be fitted with tabs 356, similar to tabs 56 in the Type IA retraction device, to enable it to be properly positioned after inflation. A similar procedure is used to deploy the Type IB retraction device in the body as is used to deploy the Type IA retraction device, and will not be described in detail. A similar inflation procedure is used, except that the additional chamber may be inflated at least partially at the same time as the first cavity is inflated. The Type IB retraction device depends more for its shape on the additional chamber than the Type IA retraction device. Hence, at least partial inflation of the additional chamber is necessary to enable the retraction device to displace organs to the side of the retraction device. Inflation pressures similar to those used for the Type IA retraction device are used.

Treatment procedures using the Type IB retraction device are similar to those using the Type IA retraction device, except that the Type IB retraction device does not provide access to tissues to the side of the device. The diaphragms 307 and 309 are analogous to the windows 46 (FIG. 1) of the Type IA retraction device. Either or both of the windows provided by the diaphragms 307 and 309 may be pierced to provide apertures though which treatment may be carried out, or through which the tissue to be treated may be brought into the retraction device for treatment, or through which instruments may be passed into and out of the main chamber 311.

7. Flexible Sheaths

A further aspect of the invention is the provision in a retraction device according to the invention, of one or more flexible sheaths to interconnect the main chamber of the retraction device and the outside of the body into which the retraction device is inserted. The flexible sheath provides a tract through the body wall that allows additional surgical instruments or endoscopes to be introduced into the main chamber of the retraction device, and/or allows tissue and the like to be removed. In one embodiment of this aspect of the invention, the flexible sheath is attached to a window of a Type I retraction device or to the main envelope of a Type II retraction device. FIG. 12A shows a flexible sheath according to the invention attached to a window 46 of a Type IA retraction device 1, which is shown as an example. A flexible sheath according to this aspect of the invention can also be used with Type IB and Type II retraction devices. The flexible sheath 3 is substantially cylindrical in shape with a closed distal end 8. The proximal end 13 of the flexible sheath is attached to the outer surface of the window 46. The sidewall 18 of the flexible sheath 3 is folded concertina-style when the retraction device is packaged, and remains folded after the retraction device has been inflated. After the retraction device 1 has been deployed in the body, as shown in FIG. 12B, a suitable pointed tool 23 is fed into the main chamber 11 to pierce a hole 28 in the part of the window 46 that is covered by the flexible sheath 3. The pointed tool 23 is pushed through the hole 28 to engage with the distal end 8 of the flexible sheath 3. The distal end 8 is first pressed against the inner surface of the body wall W using the pointed tool 23. The resulting bulge in the skin S on the outside of the body indicates where the flexible sheath 3 will emerge. A small incision 33 is made in the skin S at that point. The flexible sheath 3 is then driven by the pointed tool 23 through the body wall W to emerge through the incision 33.

With a Type I retraction device, the distal end 8 of the flexible sheath 3 is then opened to provide access to the main chamber 11. The flexible sheath does not have to be gas-tight in the manner of conventional trocar sheaths, and permits ordinary surgical instruments to be used.

With a Type II retraction device, the flexible sheath is fitted with a gas-tight port similar to the port 251 (FIG. 6) before the distal end 8 is opened.

The alternative embodiment of a flexible sheath 43 according to the invention, shown in FIG. 12C, is not initially attached to the retraction device. A Type IA retraction device 1 is shown in FIG. 12C as an example. A flexible sheath according to this aspect of the invention can also be used with Type IB and Type II retraction devices. The flexible sheath 43 comprises a cylindrical piece of flexible plastic 48 with a coaxial locking device 53 on its proximal end. The distal end of the flexible sheath for a Type II retraction device must be closed by a port (not shown) similar to the port 251 (FIG. 6) so that pressurization of the main cavity can be maintained after the flexible sheath 43 has been installed.

The flexible sheath 43 is installed after the retraction device 1 has been deployed in the body. A small incision 58 is made in the skin S of the body. The flexible sheath 43 is then driven through the body wall W by a sharp trocar point (not shown). The trocar point pierces a hole 63 in the window 46 of the retraction device 1, and pushes the locking device 53 of the flexible sheath 43 through the hole 63 to engage the locking device 53 with the window 46. When used with a Type II retraction device, the locking device 53 forms a gas-tight seal with the window 46.

8. Suction Skirt

Figure 13A:
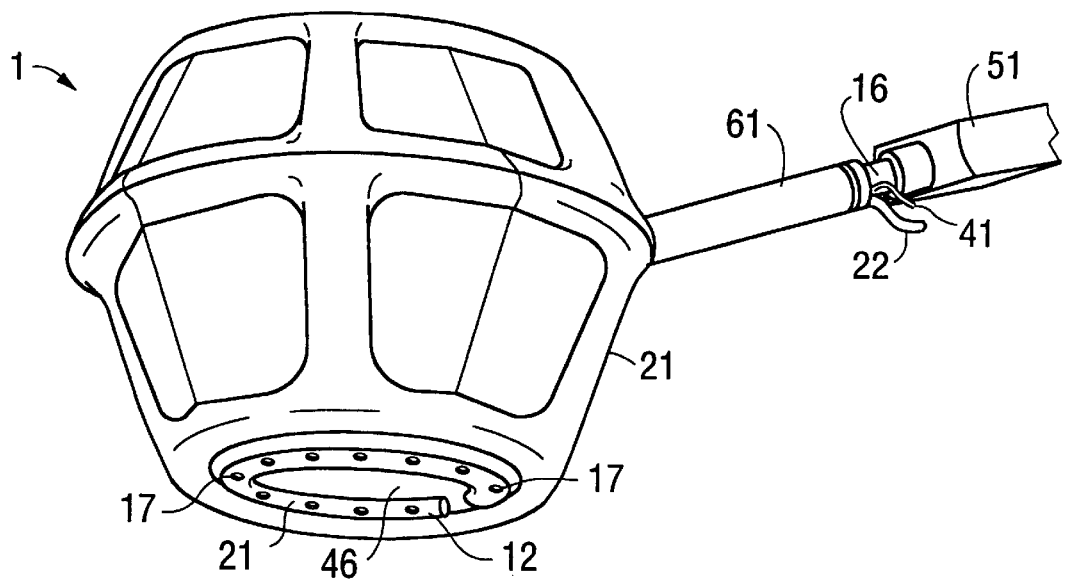
FIG. 13A is a perspective view of a polyhedral Type IA inflatable retraction device fitted with a suction skirt according to the invention.
Figure 13B:
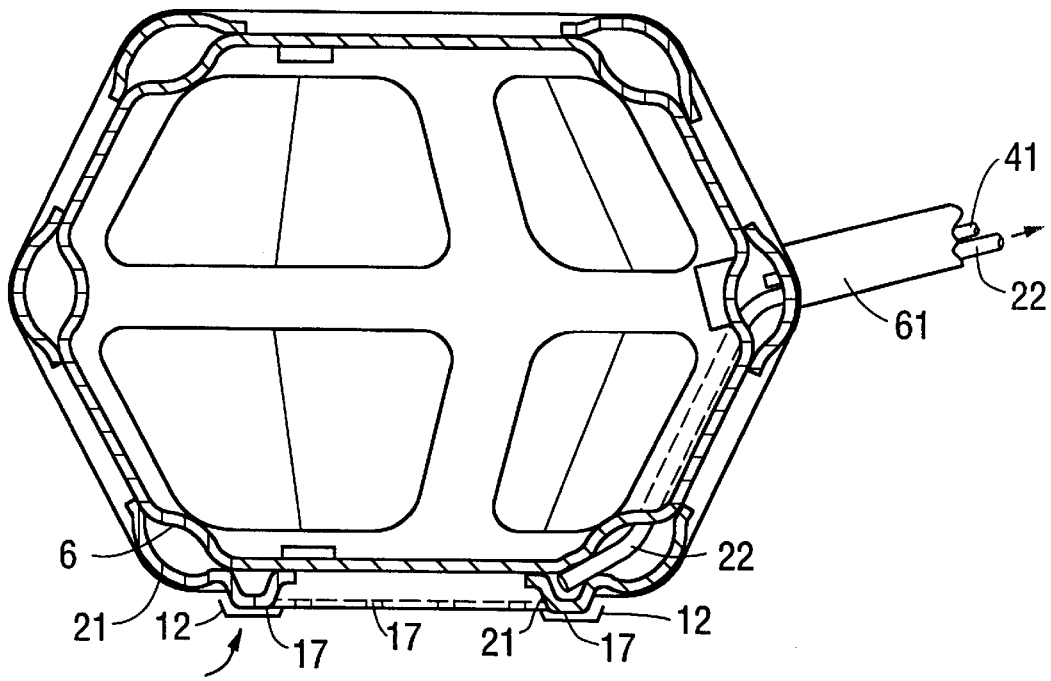
FIG. 13B is vertical cross section, along the line 2—2 in FIG. 1, of a polyhedral Type IA inflatable retraction device fitted with a suction skirt according to the invention.

According to a further aspect of the invention, a retraction device according to the invention may be fitted with a tubular suction skirt on the part of the retraction device that is lower-most when the retraction device is deployed in the body. FIGS. 13A and 13B show, as an example, a polygonal Type 1A retraction device of the type used in the abdominal cavity. The suction skirt of this aspect of the invention can be used with other type I and type II retraction devices.

Irrigation is often used during surgery to clear away bleeding or blood clots. This fluid collects in the bottom of the cavity in the body created by the retraction device and needs to be cleared away. The suction skirt 12 on the bottom of the retraction device is connected to a suction line and removes such fluid during the treatment procedure, keeping the cavity clear of accumulated fluids. In the example shown, the suction skirt is a tubular appendage attached to the lower-most extremity of the retraction device. In the retraction device shown in FIGS. 13A and 13B, the suction skirt is formed from part of the additional envelope 21 around the bottom window 46. The bottom or sides of the suction skirt is pierced with between six and twelve holes 17. In the embodiment shown, the suction skirt is about ¼" (6.2 mm) in diameter, and the holes 17 are about ⅛" (3.1 mm) in diameter.

The suction skirt is made of the polyethylene-nylon composite that is the preferred material for the main envelope 6 of the retraction device. This material is sufficiently resilient that a tubular structure made from it can retain its open cross section under a low vacuum. One end of the suction skirt is closed; the other is connected to a thin-wall polyethylene tube 22 that runs up the side of the retraction device to exit the body through the same incision as is used for the inflation tubes. If, as is shown in FIGS. 13A and 13B, the retraction device is used in an insufflated body cavity, the suction skirt tube 22 passes inside the inflation tube sheath 61. The distal end of the suction skirt tube 22 has attached to it a connector suitable for attaching to an operating room suction line.

B. Surgical Procedures Using Inflatable Retraction Devices

1. Retracting the Bowel to Provide Anterior Access to the Spine, the Aorta, the Kidneys, etc.

Figure 14A:
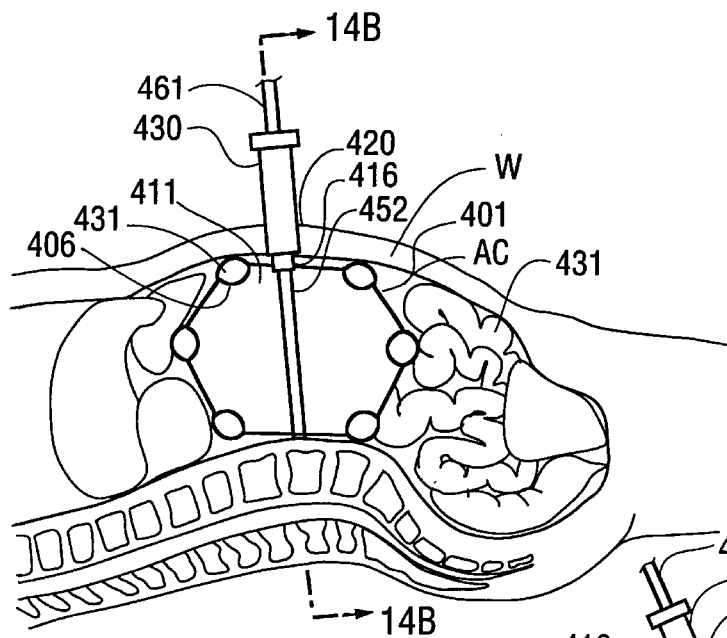
FIG. 14A is a longitudinal cross sectional elevational view of a body illustrating the use according to the invention of a retraction device according to the invention in the abdomen to retract the bowel to gain anterior access to the intravertebral discs, the aorta, or the kidneys for treatment or observation.
Figure 14B:
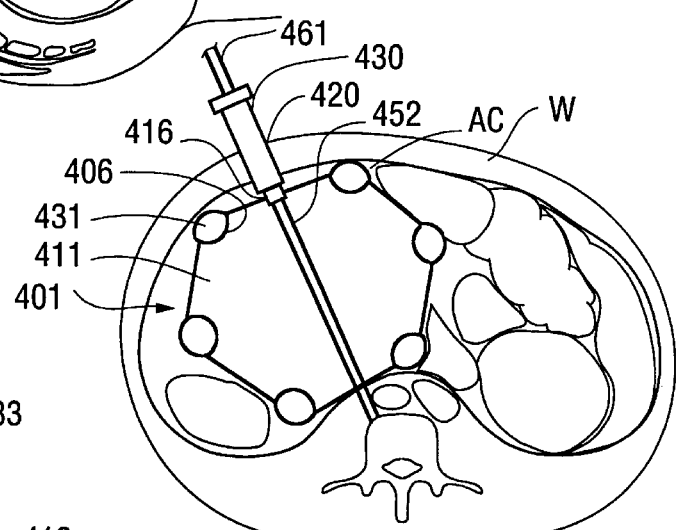
FIG. 14B is a transverse cross sectional elevational view of a body illustrating the use according to the invention of a retraction device according to the invention in the abdomen to retract the bowel to gain anterior access to the intravertebral discs, the aorta, or the kidneys for treatment or observation.

The method according to the invention of using a retraction device according to the invention in a procedure to perform an anterior resection of a herniated intervertebral disc is illustrated in FIG. 14. A method can be adapted to gain anterior access to the aorta, the kidneys, and other tissues that lie outside the peritoneum. FIG. 14A shows a longitudinal cross section of the body; and FIG. 14B shows a transverse cross section along the line 14B—14B in FIG. 14A. Anterior access to the spine is normally difficult due to the difficulty of retracting the overlying bowel using conventional laparoscopic retractors. A Type I or a Type II retraction device according to the invention is used according to the invention to retract the bowel by forming a small incision 420 in the abdominal wall W and inserting a trocar (not shown) with trocar tube 430 into the incision 420 and driving the trocar into the abdominal cavity AC. The trocar is removed and the retraction device 401 is passed through the trocar tube 430 into the abdominal cavity AC in its contracted state with the aid of its inflation tube or inflation tube shield (the inflation tube shield 461 of a Type IA retraction device is shown). After insertion and orientation, the main chamber 411 of the retraction device 401 is inflated with a suitable inflation gas passed though inflation tube 416. During the inflation process, the relatively large surface area of the main chamber 411 of the retraction device gently retracts the bowel 431, either upwards or downwards, depending on the position of the disc to be treated. The positioning of the retraction device is checked and adjusted, if necessary, as previously described.

If a Type I retraction device is used, it must be positioned such that the disc that it is desired to treat is centered in one of its windows. The additional chamber 431 is inflated, and the inflation gas pressure in the 411 main chamber is released. The inflated additional chamber maintains the shape of the retraction device.

If a Type II device is used, an elastomeric window (not shown) is installed, as previously described, on the inside of the main envelope in a position that will provide access to the disc to be treated.

The main envelope 406 of both types of retraction device can then be pierced, and partially removed, if necessary. An incision is made in the peritoneum exposed by the retraction device to gain access to and to resect the disc to be treated.

One or more flexible sheaths may be inserted through the abdominal wall to provide access to the interior of the retraction device for surgical instruments. If a Type I retraction device is used, normal surgical instruments may be used, and such tools may be freely manipulated in the space created by the retraction device. Because the main chamber of the retraction device is not under pressure, there is no need to use laparoscopic instruments through rigid trocar tubes. FIGS. 14A and 14B show instrument 452 passed from outside the body through the main inflation tube 416 into the main chamber 411. The instrument 452 passes out of the main chamber 411 through an aperture (not shown) pierced in the window 446.

Once treatment has been completed, the retraction device is deflated and removed from the body, and the small incisions in the abdominal wall repaired, as already described.

2. Retracting the Pericardium

Figure 15:
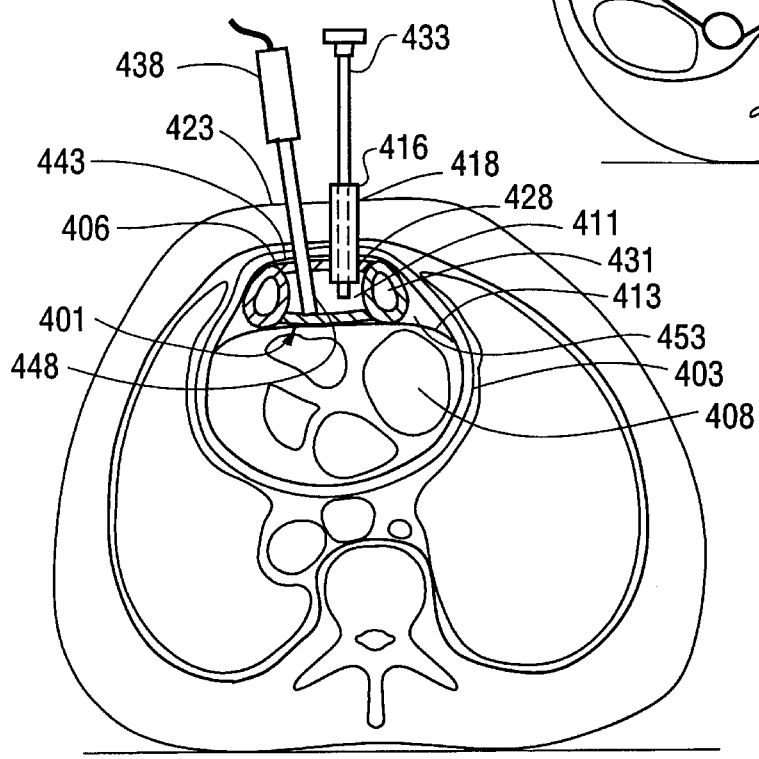
FIG. 15 is a transverse cross sectional plan view of the chest illustrating the use according to the invention of a retraction device according to the invention to retract the pericardium from the heart to gain access to the surface of the heart for treatment or observation.

A procedure according to the invention in which a small, oblate version of a Type I or Type II retraction device according to the invention is used to displace the pericardium 403 from the heart 408 is shown in FIG. 15, which shows a transverse cross section of the chest. Displacement of the pericardium allows the outer surface 413 of the heart 408 to be observed, and such procedures as endocardial mapping, ablation, transmyocardial revascularization, and defibrillation to be carried out. These procedures have until now been difficult to do laparoscopically because access to the surface of the heart 408 is obstructed by the pericardium 403.

In the procedure according to the invention, a small puncture 418 is made in the chest wall 423 and through the puncture 418, a small incision 428 is made in the pericardium 403. An introducer tube (not shown) is inserted to connect the pericardial cavity 453 to outside the patient. A retraction device 401 according to the invention is inserted using its inflation tubes (the main inflation tube 416 is shown) through the introducer tube into the pericardial cavity 453 so that it rests between the surface 413 of the heart and the pericardium 403. The retraction device 401 is then released from its packing (not shown), as described above, and its main chamber 411 is inflated. During the inflation process, the main envelope 406 of the retraction device gently displaces the heart 408 from the pericardium 403. The position of the retraction device is checked and, if necessary, adjusted.

If a Type I retraction device is used, it must be positioned such that the part of the heart that it is desired to treat is centered in one of its windows. The additional chamber 431 is then inflated and the inflation pressure removed from the main chamber.

If a Type II device is used, an elastomeric window is installed, as previously described, on the inside of the main envelope in a position that will provide access to the part of the heart to be treated.

Once the retraction device is in position, the introducer tube (not shown) can be withdrawn and the main inflation tube 416 used as a path for endoscopes and instruments to pass in to the main chamber of the retraction device.

3. Retracting the Pleura

FIG. 15 shows an endoscope 433 passed through the main inflation tube 416 to observe the outer surface 413 of the heart. FIG. 15 also shows an instrument probe 438 that has been passed through the chest wall 423 to contact the surface 413 of the heart. The instrument probe 438 is passed through the pericardium 403 and the main chamber 411 of the retraction device 401, piercing a first window 443 and a second window 448 of the retraction device. After the treatment is completed, the retraction device is withdrawn from the pericardial cavity, as already described, and the small incisions in the pericardium and the chest wall are repaired.

Figure 16A:
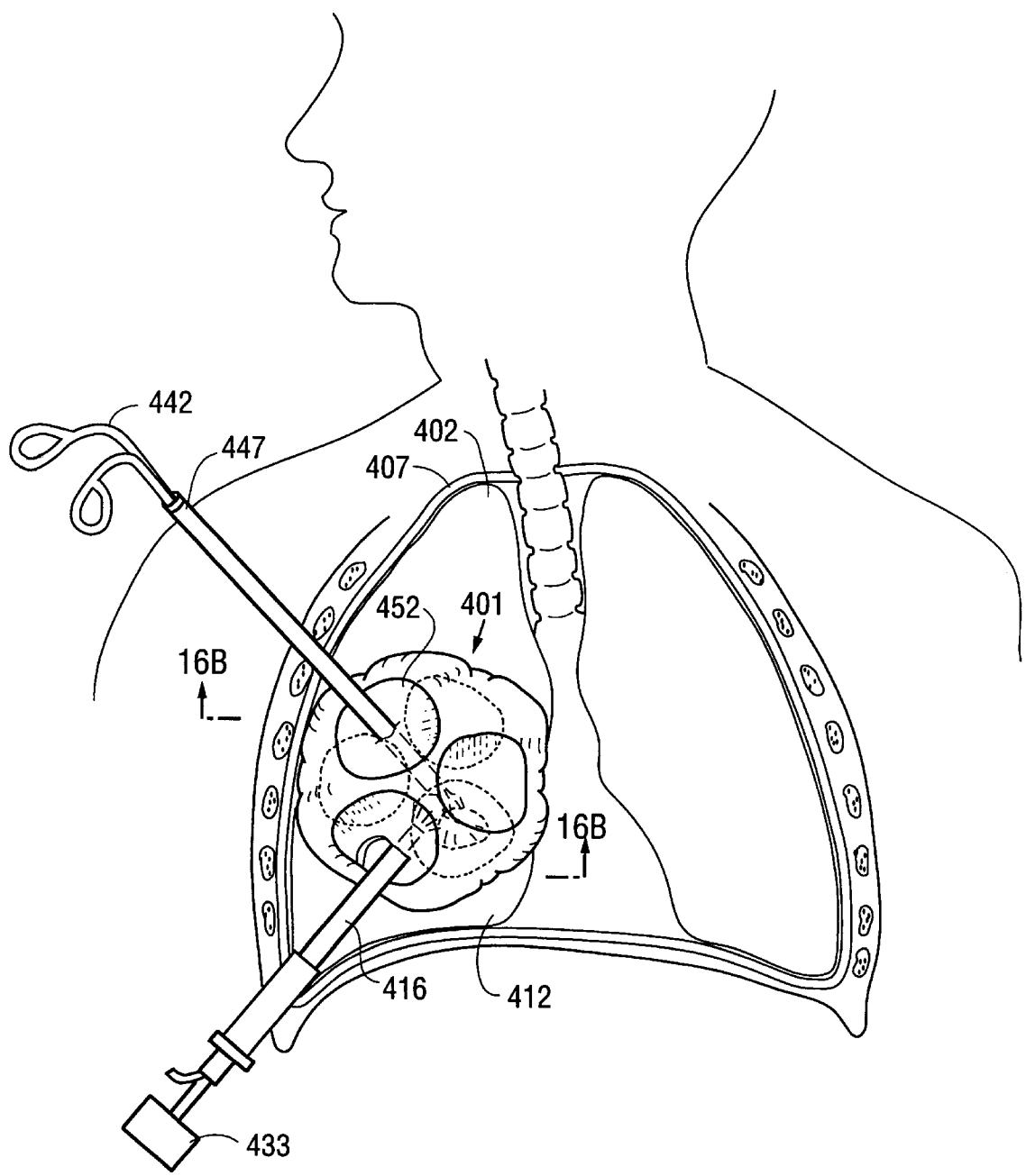
FIG. 16A is a transverse cross sectional elevational view of the chest illustrating the use according to the invention of a retraction device according to the invention to retract the lung away from the pleura to gain access to the surface of the lung for treatment or observation.
Figure 16B:
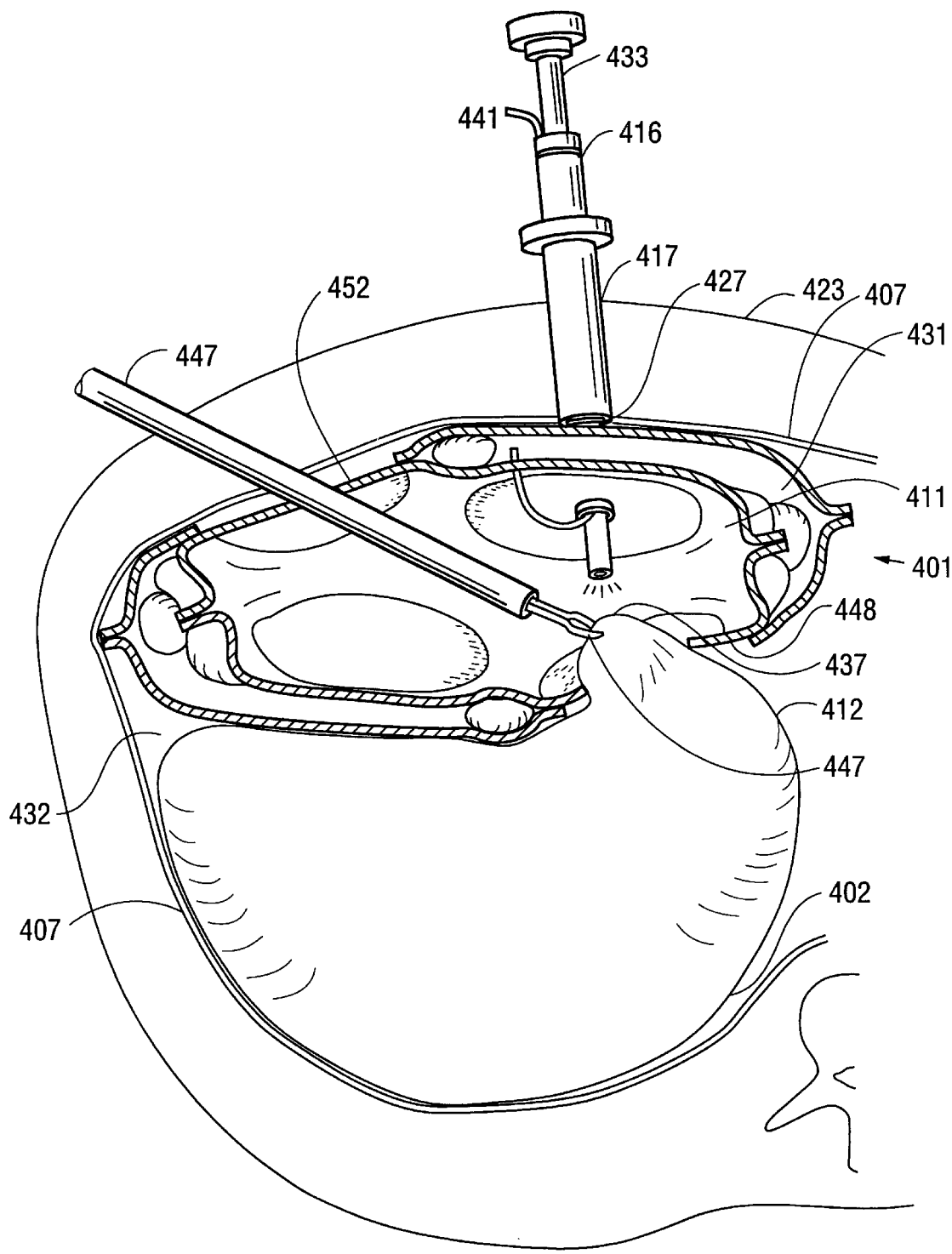
FIG. 16B is a transverse cross sectional plan view of the chest illustrating the use according to the invention of a retraction device according to the invention to retract the lung away from the pleura, part of the lung entering the main chamber of the retraction device for treatment or observation.

FIG. 16 shows a further procedure according to the invention in which a retraction device according to the invention is used in the pleural cavity to retract the lung from the pleura to allow observation and manipulation. FIG. 16A shows a vertical cross sectional view of the chest and FIG. 16B shows a transverse cross section along the line 16B—16B in FIG. 16A. A small, oblate version of a Type I or Type II retraction device 401 according to the invention is used to displace the lung 402 from the pleura 407 to allow resection of a lobe 412 of the lung 402.

In the procedure, a small incision 417 is made in the chest wall 423 and, through the incision 417, a trocar (not shown) is inserted to connect the pleural cavity 432 to outside the patient. The trocar point (not shown) is removed leaving the trocar tube (not shown) connecting the pleural cavity 432 to outside the patient. A retraction device 401 according to the invention is inserted using its inflation tubes (inflation tube 416 is shown) through the trocar tube into the pleural cavity, so that it rests between the surface of the lung 402 and the pleura 407. The retraction device 401 is then released from its packing (not shown), as described above, and its main chamber 411 is inflated. During the inflation process the main envelope 406 of the retraction device gently displaces the lung 402 from the pleura 407. The position of the retraction device is checked and, if necessary, adjusted.

If a Type I retraction device is used, it must be positioned such that the part of the lung that it is desired to treat is centered in one of its windows. The additional chamber 431 is then inflated and the inflation pressure removed from the main chamber 411.

If a Type II device is used, an elastomeric window is installed, as previously described, on the inside of the main envelope in a position that will provide access to the part of the lung to be treated.

Once the retraction device is in position, the trocar tube (not shown) can be withdrawn and the main inflation tube 416 used as a path for endoscopes and instruments to pass to the inside of the retraction device.

FIG. 16 shows an endoscope 433 passed through the main inflation tube 416 into the main chamber of the retraction device 401. In the embodiment of the retraction device 401 shown, the main inflation tube 416 enters the main chamber 411 through a first window 443. Part of a second window 448 has been removed, as already described, to allow a part 437 of the lung 402 to enter the main chamber 411 of retraction device for treatment. A trocar tube 447 passes through the chest wall 423 and enters the retraction device by piercing a third window 452, and an instrument 442 is passed through the trocar tube 447 to section part of the lung 437. The part of the window 448 that has not been removed forms a seal around the part 437 of the lung inside the retraction device, and prevents sectioned tissue from entering the pleural cavity. After the treatment of the lung is completed, the retraction device is withdrawn from the pleural cavity, as already described, and the small incisions in the pleura and the chest wall are repaired.

4. Retracting a Lobe of the Lung

In a further procedure according to the invention, a retraction device according to the invention is used to retract one lobe of a lung in a lobectomy. This is shown in FIG. 17, which shows a longitudinal cross section of the chest. The lobes of the lung overlay one another: in performing a lobectomy, access to the hilar portion of the bronchial tree is required so that the branches of the bronchial tree feeding the lobe to be sectioned can be occluded. A Type IA or Type II retraction device 401 according to the invention is used to displace the lobe 404 away from the rest of the lung 409 to provide access to the bronchial tree 414.

In the procedure, a small incision 419 is made in the chest wall 423, and through the incision 419, a trocar (not shown) is inserted through the chest wall 423 and pleura 429. The trocar (not shown) is removed and the trocar tube is maneuvered to place its distal end between the lobe 404 and the rest of the lung 409. A retraction device 401 according to the invention is inserted using its inflation tubes (inflation tube 416 is shown) through the trocar tube into position between the lobe 404 and the rest of the lung 409. The retraction device 401 is then released from its packing (not shown), as described above, and its main chamber 411 is inflated. During the inflation process, the main envelope 406 of the retraction device gently displaces the lobe 404 away from the rest of the lung 409. The position of the retraction device is checked and, if necessary, adjusted.

If a Type I retraction device is used, it must be positioned such that the part of the bronchial tree that it is desired to occlude is centered in one of its windows. The additional chamber 431 is then inflated and the inflation pressure removed from the main chamber.

If a Type II retraction device is used, a elastomeric window (not shown) is applied to the inside of the main chamber 411 in a position such that the part of the bronchial tree that it is desired to occlude can accessed through the elastomeric window.

With both types of retraction device, an aperture is cut in the main envelope 406 through which the procedure for occluding a part of the bronchial tree can be carried out using instruments, passed into the main chamber 411 through the inflation tube 416. Additional instruments can be inserted into the main chamber through flexible sheaths (not shown) and/or, in a Type I retraction device, through apertures pierced in other windows (not shown) of the main envelope 406. After the bronchial tree has been occluded, the retraction device is deflated and withdrawn, as already described, from between the lobe 404 and the rest o f the lung 409. The procedure for sectioning the lobe is carried out before the small incisions in the pleura and the chest wall are repaired.

5. Retracting the Liver to Gain Access to the Gastroesophageal Junction

An other procedure according to the invention is shown in FIG. 18. It is necessary to gain access to the gastroesophageal junction between the stomach 405 and the esophagus 410 to be able to section the vagus nerve, or to treat gastroesophageal reflux. The gastroesophageal junction is normally obscured by the liver 415, which must be retracted provide access for treating this area. A Type I or Type II retraction device 401 according to the invention is used to displace the liver 415 away from the esophagus 410. According to the procedure, a small incision 420 is made in the abdominal wall 425. A trocar (not shown) and trocar tube 440 is inserted through the incision 420 and is driven through the abdominal wall 425 into the abdominal cavity AC and the trocar is removed. The trocar tube is maneuvered to place its distal end between the liver 415 and the esophagus 410. A retraction device 401 according to the invention is inserted using its inflation tubes (inflation tube 416 is shown) through the trocar tube into position between the liver 415 and the esophagus 410. The retraction device 401 is then released from its packing (not shown), as described above, and its main chamber 411 is inflated. During the inflation process the main envelope 406 of the retraction device gently displaces the liver 415 away from the esophagus 410. The position of the retraction device is checked and, if necessary, adjusted.

If a Type I retraction device is used, it must be positioned such that the gastroesophageal junction is centered in one of its windows. The additional chamber 431 is then inflated and the inflation pressure removed from the main chamber.

If a Type II retraction device is used, a elastomeric window (not shown) is applied to the inside of the main chamber 411 in a position such that the gastroesophageal junction can accessed through the elastomeric window.

With both types of retraction device, an aperture is cut in the main envelope 406 through which the treatment procedure can be carried out using instruments (e.g., instrument 452) passed into the main chamber 411 through at least the inflation tube 416. Additionally or alternatively, instruments can be inserted into the main chamber 411 through flexible sheaths (not shown) and/or, in a Type I retraction device, through apertures pierced in other windows (not shown) in the main envelope 406. After the treatment procedure has been carried out, the retraction device is deflated and withdrawn, as already described, from between the liver 415 and the esophagus 410, the small incisions in abdominal wall are repaired.

6. Retracting the Dura Mater

Another procedure according to the invention is shown in FIG. 19, which shows a vertical cross section of the head. To observe and treat the brain 450, it is necessary to separate the brain from the overlying dura mater 455. A small, very oblate version of a Type I or Type II retraction device 401 according to the invention is used in this procedure. According to the procedure, a small incision 460 is made in the skin of the head, and, working through the incision, a small hole 465 is drilled in the skull to provide access to the dura mater 455. An incision 470 is made in the dura mater to expose the surface of the brain 450. A retraction device 401 according to the invention is inserted using forceps through the incision 460, the hole 465, and the incision 470 into the skull between the surface of the brain 450 and the dura mater 455. The retraction device 401 is then released, as described above, from its packing (not shown), and its main chamber 411 is inflated. During the inflation process the main envelope 406 of the retraction device gently displaces the brain 450 away from the dura mater 455. The position of the retraction device is checked and, if necessary, adjusted.

If a Type I retraction device is used, it must be positioned such that part of the brain that it is desired to treat is centered in one of its windows. The additional chamber (not shown) is then inflated and the inflation pressure removed from the main chamber.

If a Type II retraction device is used, a elastomeric window (not shown) is applied to the inside of the main chamber 411 in a position such that the part of the brain that it is desired to treat can be accessed through the elastomeric window.

With both types of retraction device, an aperture is cut in the main envelope 406 through which the treatment procedure can be carried out, using instruments passed into the main chamber 411 through the inflation tube 416. Additionally or alternatively, instruments can be inserted into the main chamber, in a Type I retraction device, through apertures pierced in other windows (465, 470) of the main envelope 406. After the treatment procedure has been carried out, the retraction device is deflated and withdrawn, as already described, from between the brain 450 and the dura mater 455. Finally, the small incisions in the dura mater and the scalp and the hole in the skull are repaired.

7. Hernia Repair

Laparoscopic techniques are already being used to repair hernias, but conventional techniques require that two incisions be made in the peritoneum, the second incision being a relatively large one, and the peritoneum around the second incision be retracted. These unnecessary incisions delay recovery and provide the opportunity for complications. A procedure according to the invention enables hernia repair to be carried out without having to breach the peritoneum. FIG. 20A shows a vertical cross section of the lower abdomen. A flat, substantially elliptical or rectangular Type IA or Type II retraction device 501 according to the invention is used to retract the peritoneum 502 away from the abdominal wall 517. In the procedure according to the invention, a small incision 522 is made in the abdominal wall 517 near the umbilicus 507, and the layers of tissue are cut through as far as the peritoneum. A retraction device 501 according to the invention is inserted using forceps through the incision 522 into position between the abdominal wall 517 and the peritoneum 502. The retraction device 501 is then released, as described above, from its packing (not shown), and its main chamber 511 is inflated. During the inflation process the main envelope 506 of the retraction device spreads inferiorly towards the inguinal area, and gently displaces the peritoneum 502 back from the abdominal wall 517. The position of the retraction device is checked and, if necessary, adjusted.

If a Type I retraction device is used, it must be positioned such that the site of the hernia is centered in one of its windows. The additional chamber 531 is then inflated and the inflation pressure removed from the main chamber.

If a Type II retraction device is used, a elastomeric window (not shown) is applied to the inside of the main chamber 511 in a position such that the site of the hernia can be accessed through the elastomeric window.

With both types of retraction device, an aperture is cut in the main envelope 506 through which the treatment procedure can be carried out using instruments passed into the main chamber 511 through the inflation tube 516. Additionally or alternatively, instruments can be inserted into the main chamber through flexible sheaths (not shown) and/or, in a Type I retraction device, through apertures (not shown) pierced in other windows of the main envelope 506. After the hernia has been repaired, the retraction device is deflated and withdrawn, as already described, from between the peritoneum 502 and the abdominal wall 517 and the small incision in the abdominal wall 517 is repaired.

One known technique for repairing a hernia is by suturing or stapling a fine mesh over the site of the hernia. The mesh is preferably installed on the abdominal wall outside the peritoneum to prevent the mesh and its sutures or staples from irritating the bowel. Using conventional laparoscopic techniques to hold the mesh in place while it is cut to size and stapled in position is a very difficult procedure. In a procedure according to the invention, a piece of mesh 527 is attached, for instance by a suitable adhesive applied to the perimeter of the piece of mesh, to substantially cover the window 532 of the retraction device 501, as shown in FIG. 21. The window 532 is the window that will contact the site of the hernia 512 when the retraction device has been deployed. The retraction device with the mesh is then packaged as previously described, and the retraction device is inserted between the peritoneum 502 and the abdominal cavity 517 and inflated, also as previously described. Inflation of the balloon causes flattening and/or expansion of the mesh into the condition shown in FIG. 21.

The position of the retraction device 501 is then adjusted, using tabs 556 and a suitable gripping tool (not shown) to position the mesh-covered window so that the mesh 527 covers the site of the hernia 512. Once the retraction device is properly positioned, the additional chamber 531 is inflated and the inflation pressure removed from the main chamber. The retraction device 501 holds the mesh 527 in place over the site of the hernia while the mesh is stapled in place and excess mesh is cut off. Part of the window 532 is cut away, using a suitable tool inserted into the main chamber 511 through the inflation tube 516, to expose the area of the mesh into which staples will be placed. The mesh is stapled to the site of the hernia 512 using staples (not shown) inserted by means of a conventional laparoscopic stapler (not shown). More of the window 532 is then cut away and a suitable laparoscopic cutting tool is inserted into the main chamber 511 to cut the mesh around the stapled area. The excess mesh is removed when the retraction device is removed from the body, as previously described.

In a variation on this procedure, a low irritation Dacron® mesh is installed on the inside of the peritoneum, the retraction device with a piece of mesh covering one of its windows being inserted into the peritoneal cavity before the retraction device is inflated, as shown in FIG. 20B.

In a variation on both of the above procedures, the mesh is cut to the required size before it is attached to the window of the retraction device. The mesh is attached to the window of the retraction device by one-pull lacing, and the thread for the one-pull lacing is fed through the main inflation tube. After the mesh has been correctly positioned and stapled in place, as previously described, the thread is pulled to release the one-pull lacing, which releases the mesh from the window of the retraction device. The retraction device is then withdrawn as previously described. This variation does not require the mesh to be cut to size after it has been stapled in place.

C. Methods of Construction Inflatable Retraction Devices

1. Polygonal Type IA Retraction Device

The construction according to the invention of a polygonal Type IA retraction device is illustrated in FIGS. 22A and 22B. The construction of a dodecahedral retraction device is illustrated. A dodecahedral retraction device gives a good compromise between approximating a spherical or spheroidal shape, and complexity. Increasing the number of faces makes a shape that is more nearly spherical but is more complex to make. The additional chamber of a retraction device that is more nearly spherical provides more retraction force than the additional chamber of a polyhedral retraction device that is more nearly cubic.

The main envelope and the additional envelope of the retraction device are both made of a relatively inelastic and tough film of a plastic such as Mylar®, polyethylene, or polyurethane. The preferred material is a polyethylene and nylon composite. The thickness of the main envelope is typically from 0.5 to 5 mils (13 to 130 microns). In the preferred embodiment, the additional envelope is made from a film of the same thickness of the same plastic as the main envelope. However, in some applications it may be advantageous make the additional envelope from a film of a different thickness of the same plastic, or from a film of the same or a different thickness of a different plastic.

Two segmented circular main envelope blanks 600 and 601 and two segmented circular additional envelope blanks 625 and 626 are cut from a piece of film, preferably by die cutting.

The main envelope blank 600, the additional envelope blank 625, and the formation of an envelope half from them will now be described. A similar explanation applies to the main envelope blank 601, the additional envelope blank 626, and the formation of an envelope half from them.

The number of segments in the two main envelope blanks 600 and 601, plus 2, determines the number of faces that the polyhedral retraction device will have. In the dodecahedral retraction device illustrated, the main envelope blank 600 has five segments 605. The width and depth of the segments 605 determines the shape of the retraction device: wide, shallow segments result is a relatively flat retraction device, whereas narrow, deep segments result in a relatively tall retraction device.

The number of segments 630 in the additional envelope blank 625 is preferably equal to the number of segments 605 of the main envelope blank 600; thus, the additional envelope blank 625 has five segments 630 to match the five segments 605 of the main envelope blank 600. The shape of the segments 630 is substantially the same as that of the segments 605, except the parts of each segment 630 indicated by shading and the reference numeral 655 in FIG. 22B are cut away compared with the segment 605 in the main envelope blank. When the additional envelope blank 625 is assembled with the main envelope blank 600, the cut away areas 655 provide the windows 46 (FIG. 1) in the side of the retraction device. Each area 655 will therefore be called a side window area 655. Another area 645 in the center of the additional envelope blank 625 is cut away. When the additional envelope 625 is assembled with the main envelope blank 600, the cut away area 645 forms the window 46 (FIG. 1) in the top end or the bottom end of the retraction device, and will thus be called the end window area 645. The end window area is shown with a circular shape in FIG. 22B; alternatively, it could have a polygonal shape. The side and end window areas are preferably cut in the same die-cutting operation in which the additional envelope is die cut from the plastic film.

An envelope half is made by laying the additional envelope blank 625 on the main envelope blank 600 such that the segments 630 coincide with the segments 605. The broken line 650 in FIG. 22A indicates the position of each side window area 655 when the additional envelope blank 625 is correctly positioned on the main envelope bank 600. The periphery of each side window area 655 of the additional envelope blank 625 is attached to the main envelope blank 600, preferably by welding. Alternatively, a line of adhesive applied to the periphery of each side window area 655 can be used. The periphery of the end window area 645 in the additional envelope blank 625 is also attached to the main envelope blank 600, preferably by welding. Alternatively, a line of adhesive applied to the periphery of the end window area 645 can be used.

The envelope half is then given a 3-dimensional form by joining the edge 610 of each segment 605 in the main envelope blank 600 to the edge 615 of the adjacent segment, and by joining the edge 635 of each segment 630 in the additional envelope blank 625 to the edge 640 of the adjacent segment. The preferred method of joining in this step and the following steps involving joining is overlap welding. Alternatively, butt welding or a line of a suitable adhesive can be used. The envelope half may be formed so that the additional envelope blank 625 is inside or outside the main envelope blank 600. In the preferred embodiment, the additional envelope blank is inside the main envelope blank.

A second envelope half is made from the main envelope blank 601 and the additional envelope blank 626, as described above. One of the two envelope halves is then inverted relative to the other, and the two envelope halves are joined together with the periphery 620 in contact with the periphery 621 (main envelope) and the periphery 660 in contact with the periphery 661 (additional envelope). The peripheries of the envelope blanks on the inside are joined first. In the preferred embodiment, which has the additional envelope outside the main envelope, the envelope halves are joined as follows: the peripheries 620 and 621 of the main envelope blanks 600 and 601 are joined first. A small part of the peripheries 620 and 621 of the main envelope blanks is left unjoined. The main inflation tube 616 is a piece of polyethylene tubing with an outside diameter in the range of 2.5 to 19.5 mm (0.1" to 0.77") and of suitable length. The distal end of the main inflation tube 616 is fitted with a port 651 that allows surgical instruments to be passed into the main inflation tube while maintaining inflation pressure in the main chamber of the retraction device. The port 651 also includes a fitting (not shown) suitable for connecting the port to a source of inflation gas (not shown). The proximal end of the main inflation tube 616 is inserted into the unjoined part of the peripheries 620 and 621 of the additional envelope blanks 600 and 601 and joining the periphery 620 to the periphery 621 is completed. Where the peripheries 620 and 621 contact the main inflation tube 616, they are joined to the outer wall of the main inflation tube to form a gas-tight seal.

The peripheries 660 and 661 of the outer envelope blanks, i.e., the additional envelope blanks 625 and 626, are then joined to one another and, where they contact the main inflation tube 616, to the outer wall of the main inflation tube to form a gas-tight seal. A small part of the peripheries 660 and 661 of the additional envelope blanks 625 and 626 is left unjoined. The additional inflation tube 641 is a piece of polyethylene tubing with an outside diameter in the range of 2.5 to 5 mm (0.1" to 0.2") and of suitable length. The distal end of the additional inflation tube 641 is fitted with a fitting (not shown) suitable for connecting it to a source of inflation gas (not shown). The proximal end of the additional inflation tube 641 is inserted into the unjoined part of the peripheries 660 and 661 of the additional envelope blanks 625 and 626, and joining the periphery 660 to the periphery 661 is completed. Where the peripheries 660 and 661 contact the additional inflation tube 641, they are joined to the outer wall of the additional inflation tube to form a gas-tight seal.

In the alternative embodiment, with the additional envelope inside the main envelope, the peripheries 660 and 661 of the additional envelope blanks 625 and 626 are joined to one another and to the outer wall of the main inflation tube 616. The peripheries 620 and 621 of the main envelope blanks 600 and 601 are then joined together, and to the outer wall of the main inflation tube 616 and to the outer wall of the additional inflation tube 641.

If the retraction device is for use in an insufflated body cavity, the main and additional inflation tubes must be surrounded by an inflation tube shield. The additional envelope blanks for such a retraction device are cut to include an inflation tube seal 680 and 681. The inflation tube sheath (not shown) is pushed over the main and additional inflation tubes after they have been sealed into the retraction device and the inflation tube seals are joined to one another, preferably by welding. Alternatively, a suitable adhesive can be used. Where the inflation tube seals 680 and 681 contact the inflation tube sheath, they are joined to the outer wall of the inflation tube shield to form a gas-tight seal. The above method can be adapted for use if a single extrusion is used to provide the main and additional inflation tubes and the inflation tube sheath.

An alternative method of making a polygonal type IA retraction device is the same as the method just described, except that the additional envelope blanks 625 and 626 are cut with the same die as the main envelope blanks 600 and 601. A main envelope blank is attached to an additional envelope blank by welding along the broken lines 650 and 665 (FIG. 22A). Alternatively, a main envelope blank can be attached to an additional envelope blank by a line of a suitable adhesive spread along the broken lines 650 and 665. The envelope halves are then formed and attached to one another using the method described above.

The additional chamber of a retraction device in which the additional envelope blank and the main envelope blank are cut using the same die is substantially the same shape as the additional chamber of a retraction device in which the additional envelope blank is cut using its own die. The alternative method of construction saves the tooling cost of the die to cut the additional envelope blank. A retraction device made according to this method has a double thickness of film on its windows 46 (FIG. 1), which makes it somewhat more difficult to cut apertures in the windows prior to carrying out the treatment process.

2. Polygonal Type IA Retraction Device with Suction Skirt

Figure 23A:
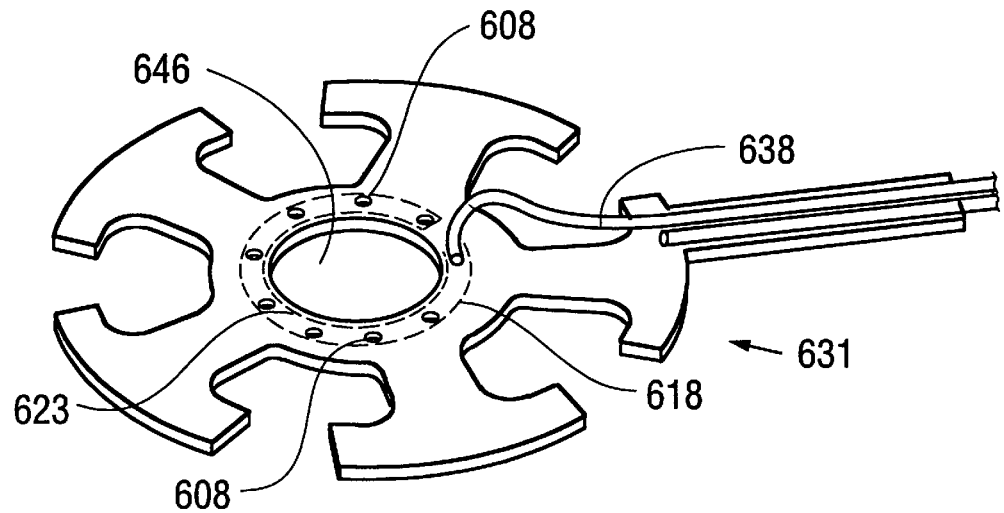
FIG. 23A is a perspective view of the additional envelope blank of a polygonal Type IA retraction device showing how a suction skirt according to the invention is formed from the additional envelope blank.
Figure 23B:
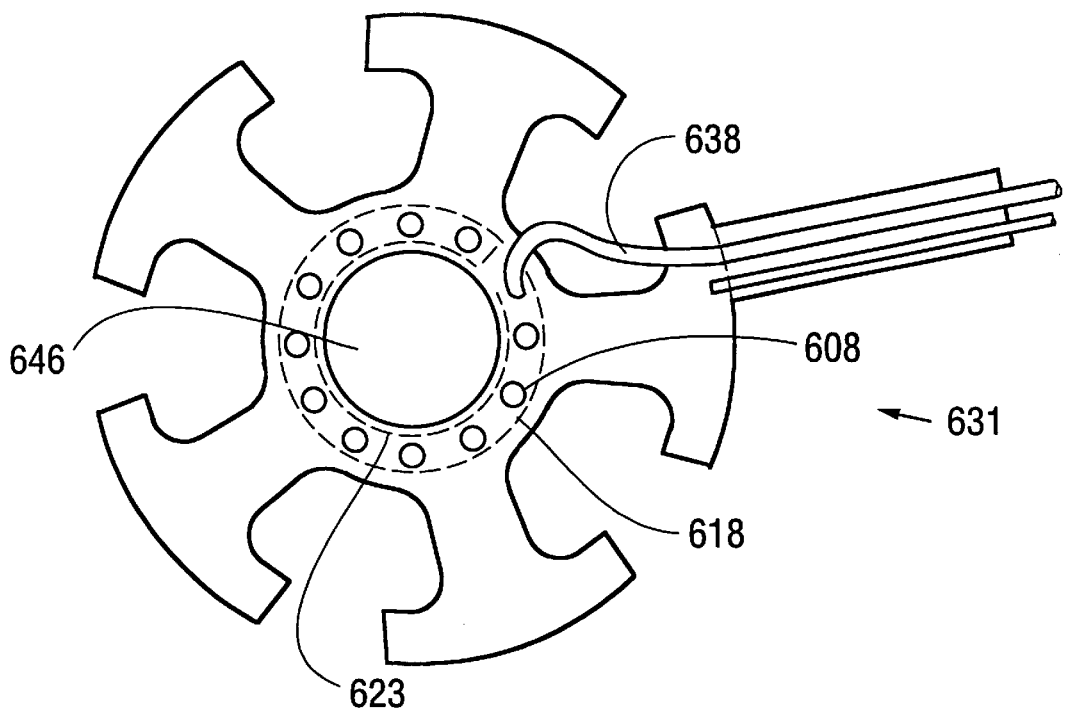
FIG. 23B is a plan view of the additional envelope blank of a polygonal Type IA retraction device showing how a suction skirt according to the invention is formed from the additional envelope blank.

The construction according to the invention of a polygonal Type IA retraction device including a suction skirt according to the invention is illustrated in FIGS. 23A and 23B. A plurality of holes 608, preferably between 6 and 12, are cut around the periphery of the end window area 646 of the additional envelope blank 631. Each hole 608 is preferably about ⅛" (3 mm) in diameter. When the retraction device is deployed in the body, it must be oriented such that the additional envelope blank 631 is lower-most. Additionally, a short radial cut 613 is made in the additional envelope blank 631. Preferably, the holes 608 and the radial cut 613 are die cut, preferably by the same die used to cut the additional envelope blank 631.

The method of constructing the retraction device is the same as that described above, except that the step of attaching the periphery of the end window 646 of the additional envelope blank 631 to the main envelope blank 601 is changed as follows: additional envelope blank 631 is attached to the main envelope blank 601 by welding along a circular line concentric with the end window area 646 and displaced radially outward by about 0.5" (12.5 mm) to lie outside the line of the holes 608. The weld line is indicated in FIG. 23 by the broken line 618. The part of the additional envelope blank 631 forming the periphery of the end window area 646 is then displaced radially outwards by about ⅛" (3 mm) and is attached to the main envelope blank 601 by a circular weld, indicated by the broken line 623, inside the line of the holes 608. Displacing the periphery of the end window area radially outward moves the part of the additional envelope blank 631 between the two welds indicated by the broken lines 618 and 623 away from the part of the main envelope blank that it overlays, and forms a flat tubular structure between the two envelope blanks. One end of the tubular structure is closed by a short radial weld indicated by the broken line 633, close to the radial cut 613.

Construction of the retraction device is completed as described above. The proximal end of the suction tube 638, which is a piece of thin-wall polyethylene tubing about ¼" (6 mm) in outside diameter is inserted into the open end of the tubular structure provided by the radial cut 613. In a retraction device for use in an insufflated body cavity, the suction tube 638 is sealed into the inflation tube sheath.

The method described above can be adapted to provide a suction skirt around one of the side windows of a polygonal Type IA retraction device. Such a suction skirt would be useful if the retraction device is oriented with a side window lower-most when in use. The method can also be adapted to make a flat retraction device with a suction skirt around one or more of its holes or around the junction between its envelope halves. The method can also be adapted to make a triangular prism-shaped Type IA retraction device with a suction skirt around one of its holes or along one or both of the sides of its lower-most face.

3. Relatively Flat Type IA Retraction Device

The construction according to a further aspect of the invention of a simpler, relatively flat Type IA retraction device according to the invention is illustrated in FIGS. 24A and 24B. The main envelope and the additional envelope of the retraction device are both made of a relatively inelastic and tough film of a plastic such as Mylar®, polyethylene, or polyurethane. The preferred material is a polyethylene and nylon composite. The thickness of the main envelope is typically from 0.5 to 5 mils (13 to 130 microns). In the preferred embodiment, the additional envelope is made from a film of the same thickness of the same plastic as the main envelope. However, in some applications it may be advantageous make the additional envelope from a film of a different thickness of the same plastic, or from a film of the same or a different thickness of a different plastic.

Two substantially circular or elliptical main envelope blanks 600 and 601, substantially equal in size, and two substantially circular or elliptical additional envelope blanks 625 and 626, substantially the same size as the main envelope blanks 600 and 601, are cut from a piece of film, preferably by die cutting. The die cutting process also cuts holes 670 and 671 in the additional envelope blanks 625 and 626 respectively. The number, shape, and size of holes 670 and 671 depends on the intended application of the retraction device. When the additional envelope blanks 625 and 626 are assembled with the main envelope blanks 600 and 601 respectively, the holes 670 and 671 form the windows 646 (FIG. 24B) in the retraction device. Increasing the proportion of the additional envelope removed to form holes 670 and 671 increases the window area through which treatment procedures can be carried out, but reduces the ability of the additional cavity of the retraction device to maintain retraction after the main cavity has been punctured.

An envelope half is made by laying the additional envelope blank 625 on the main envelope blank 600. The positions of the periphery of each hole 670 when the additional envelope blank 625 is properly positioned on the main envelope bank 600 is indicated by the broken line 650 in FIG. 24A. The periphery of each hole 670 of the additional envelope blank 625 is attached to the main envelope blank 600, preferably by welding. Alternatively, a line of adhesive applied to the periphery of each hole 670 can be used. A second envelope half is made from the main envelope blank 601 and the additional envelope blank 626, using the method described above.

One of the two envelope halves is then inverted relative to the other, and the two envelope halves are joined together with the periphery 620 in contact with the periphery 621 (main envelope) and the periphery 660 in contact with the periphery 661 (additional envelope). The envelope halves may be joined such that the additional envelope blanks 625 and 626 are inside or outside the main envelope blanks 600 and 601. In the preferred embodiment, the additional envelope blanks are inside the main envelope blanks. The method of joining the envelope halves is the same as the method for joining the envelope halves of a polygonal Type IA retraction device, so will not be further described. The completed retraction device is shown in FIG. 24B.

In an alternative embodiment of the relatively flat Type IA retraction device, the main inflation tube may be connected to the main chamber by piercing a hole in one of the windows 646 and attaching the periphery of the hole to the outer wall of the inflation tube. This embodiment is more useful than the basic embodiment, in which the main inflation tube is connected between the perimeters of the two envelope halves, in procedures in which the convenient entry point in the body for instruments lies more or less directly across the short dimension of the retraction device from the tissue to be treated. Examples of such procedures are shown in FIGS. 15, 16A, 16B, and 19.

In the alternative embodiment with the additional envelope outside the main envelope, the peripheries 620 and 621 of the main envelope blanks are joined to one another and to the outer wall of the main inflation tube. The peripheries 660 and 661 of the additional envelope blanks are then joined to one another, and to the outer walls of the main and the additional inflation tubes.

The flat Type IA retraction device can also be made with its additional envelope blanks and its main envelope blanks cut using the same die, as described in connection with the polygonal Type IA retraction device. The main and additional envelope blanks are attached by welding or a line of adhesive along the broken lines 650.

4. Triangular Prism-Shaped Type IA Retraction Device

The triangular prism Type IA retraction device is constructed according to the invention from two flat envelope blanks, as shown in FIG. 25C. The main envelope and the additional envelope of the retraction device are both made of a relatively inelastic and tough film of a plastic such as Mylar®, polyethylene, or polyurethane. The preferred material is a polyethylene and nylon composite. The thickness of the main envelope is typically from 0.5 to 5 mils (13 to 130 microns). In the preferred embodiment, the additional envelope is made from a film of the same thickness of the same plastic as the main envelope. However, in some applications it may be advantageous make the additional envelope from a film of a different thickness of the same plastic, or from a film of the same or a different thickness of a different plastic.

A substantially rectangular main envelope blank 700, and a substantially rectangular additional envelope blank 725, substantially the same size as the main envelope blank 700, are cut from a piece of film, preferably by die cutting. Each envelope blank 700 and 725 can be regarded as being divided lengthwise into three panels. At least-the two outer panels have equal length. Each panel is serrated as shown in FIG. 25C. If the outer panels are larger than the inner panel, their serrations are truncated, as shown. The serrations are preferably die cut at the same time as the envelope panels are die cut. The die cutting process also cuts one hole 770 in each panel of the additional envelope blank 725, as shown in FIG. 25D. Substantially circular holes are shown in FIG. 25D: holes of a different shape, or more than one hole per panel can be cut, depending on the intended application of the retraction device. When the additional envelope blank 725 is assembled with the main envelope blank 700, the holes 770 form the windows 746 (FIG. 25A) in the retraction device. Increasing the proportion of the additional envelope removed to form the holes 770 increases the window area through which treatment procedures can be carried out, but reduces the ability of the additional cavity of the retraction device to maintain retraction after the main cavity has been punctured.

Assembly is begun by laying the additional envelope blank 725 on the main envelope blank 700 so that their peripheries overlap. The positions of the periphery of each hole 770 when the additional envelope blank 725 is properly positioned on the main envelope bank 700 is indicated by the broken line 750 in FIG. 25C. The periphery of each hole 770 of the additional envelope blank 725 is joined to the main envelope blank 700. The preferred method of joining in this step and the following steps involving joining is overlap welding. Alternatively, a line of adhesive applied to the periphery of the pieces being joined, for example, the periphery of each hole 770, can be used. The periphery 760 of the additional envelope blank 725 is joined to the periphery 720 of the main envelope blank 700 by welding along the broken line 740. A small part of the peripheries 720 and 760 is left unjoined.

The additional inflation tube 741 is a piece of polyethylene tubing with an outside diameter in the range of 2.5 to 5 mm (0.1" to 0.2") and of suitable length. The distal end of the additional inflation tube 741 is fitted with a fitting (not shown) suitable for connecting it to a source of inflation gas (not shown). The proximal end of the additional inflation tube 741 is inserted into the unjoined part of the periphery 720 of the main envelope blank 700 and the periphery 760 of the additional envelope blank 725, and joining the periphery 720 to the periphery 760 is completed. Where the peripheries 720 and 760 contact the additional inflation tube 741, they are joined to the outer wall of the additional inflation tube to form a gas-tight seal.

The retraction device is then folded, as shown by the arrows 782 and 787, along the boundaries between the panels, i.e., along the lines 710 and 715, to bring edge 722 into contact with edge 727 with the main envelope blank 700 on the inside. The following parts of the periphery of the retraction device are then joined: 736 to 741, 737 to 742, 746 to 751, 747 to 752, 756 to 761, 757 to 762, 766 to 771, 767 to 772, and 722 to 727. A small part of the peripheries 722 and 727 is left unjoined.

The main inflation tube 716 is a piece of polyethylene tubing with an outside diameter in the range of 2.5 to 19.5 mm (0.1" to 0.77") and of suitable length. The distal end of the main inflation tube 716 is fitted with a port (not shown) that allows surgical instruments to be passed into the main inflation tube while maintaining inflation pressure in the main chamber of the retraction device. The port also includes a fitting (not shown) suitable for connecting the port to a source of inflation gas (not shown). The proximal end of the main inflation tube 716 is inserted into the unjoined part of the peripheries 722 and 727 and joining the periphery 722 to the periphery 727 is completed. Where the peripheries 722 and 727 contact the main inflation tube 716, they are joined to the outer wall of the main inflation tube to form a gas-tight seal.

If the retraction device is for use in an insufflated body cavity, the main and additional inflation tubes must be surrounded by an inflation tube shield. The main and additional envelope blanks for such a retraction device are each cut to include an inflation tube seal 780 and 781. The inflation tube sheath (not shown) is pushed over the main and additional inflation tubes after they have been sealed into the retraction device and the peripheries of the inflation tube seals are joined to one another. Where the inflation tube seals 780 and 781 contact the inflation tube sheath, they are joined to the outer wall of the inflation tube shield to form a gas-tight seal. The above method can be adapted for use if a single extrusion is used to provide the main and additional inflation tubes and the inflation tube sheath.

The triangular prism-shaped Type IA retraction device can also be made with its additional envelope blank and its main envelope blank cut using the same die, as described in connection with the polygonal Type IA retraction device. The additional envelope blank is attached to the main envelope blank by welding or a line of adhesive along the broken lines 750.

5. Polygonal Type II Retraction Device

Figure 26:
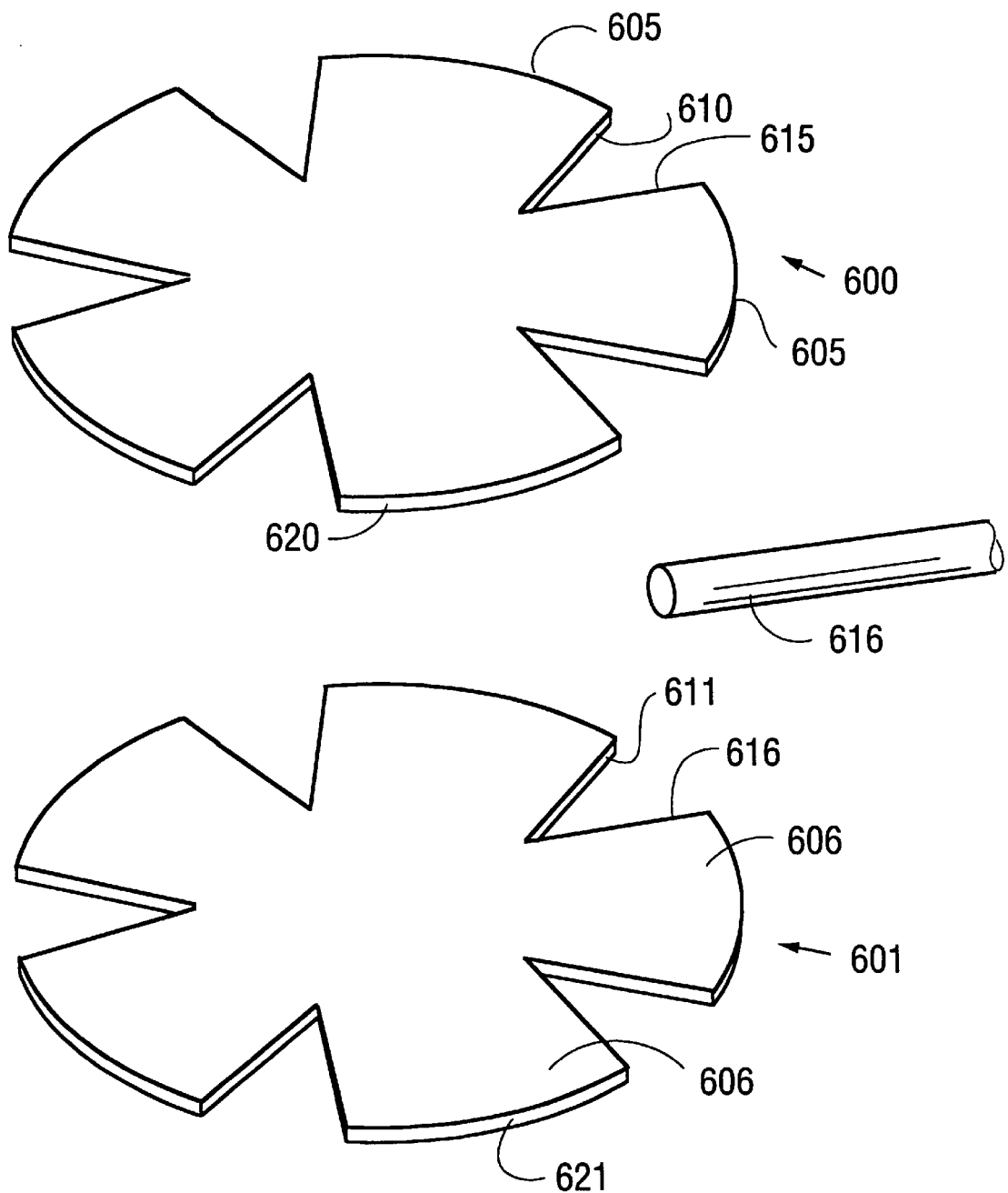
FIG. 26 is an exploded perspective view of the components of a polygonal Type II retraction device illustrating the construction of such a device according to the invention.

The construction according to the invention of a polygonal Type II retraction device is illustrated in FIG. 26. The construction of a dodecahedral retraction device is illustrated. A dodecahedral retraction device gives a good compromise between approximating a spherical or spheroidal shape, and providing windows of a useful size. Increasing the number of faces makes a shape that is more nearly spherical but has smaller faces, which limits the size of elastomeric window that can be used.

The main (and only) envelope of the Type II retraction device is made of a relatively inelastic and tough film of a plastic such as Mylar®, polyethylene, or polyurethane. The preferred material for the main envelope is a polyethylene and nylon composite. The thickness of the main envelope is typically from 0.5 to 5 mils (13 to 130 microns). To form the main envelope, two segmented circular main envelope blanks 600 and 601 are cut from a piece of film, preferably by die cutting. The number of segments 605 in the two main envelope blanks 600 and 601, plus 2, determines the number of faces that the polyhedral retraction device will have. In the dodecahedral retraction device illustrated, the main envelope blanks 600 and 601 each have five segments 605. The width and depth of the segments 605 determines the shape of the retraction device: wide, shallow segments result is a relatively flat retraction device, whereas narrow, deep segments result in a relatively tall retraction device.

An envelope half is formed by joining the edge 610 of each segment 605 in the main envelope blank 600 to the edge 615 of the adjacent segment. The preferred method of joining is overlap welding, but butt welding or a suitable adhesive can also be used. A second envelope half is made using the main envelope blank 601. One of the two envelope halves is then inverted relative to the other, and the two envelope halves are joined together with the periphery 620 in contact with the periphery 621. Again, the preferred method of joining is overlap welding, but butt welding or a suitable adhesive can also be used. A small part of the peripheries 620 and 621 of the two main envelope blanks 600 and 601 is left unjoined.

The main inflation tube 616 is a piece of polyethylene tubing with an outside diameter in the range of 2.5 to 19.5 mm (0.1" to 0.77") and of suitable length. The distal end of the main inflation tube 616 is fitted with a port 651 that allows surgical instruments to be passed into the main inflation tube while maintaining inflation pressure in the main chamber of the retraction device. The proximal end of the main inflation tube 616 is inserted into the unjoined part of the peripheries 620 and 621 and joining the periphery 620 to the periphery 621 is completed. Where the peripheries 620 and 621 contact the inflation tube 616, they are joined to the outer wall of the inflation tube such that a gas-tight main envelope is formed in contact with the bore of the main inflation tube.

The methods described above for making relatively flat and triangular prism-shaped Type IA retraction devices can easily be adapted to make relatively flat and triangular prism-shaped Type II retraction devices respectively.

6. Curved Type IA and Type II Retraction Devices

Figure 27:
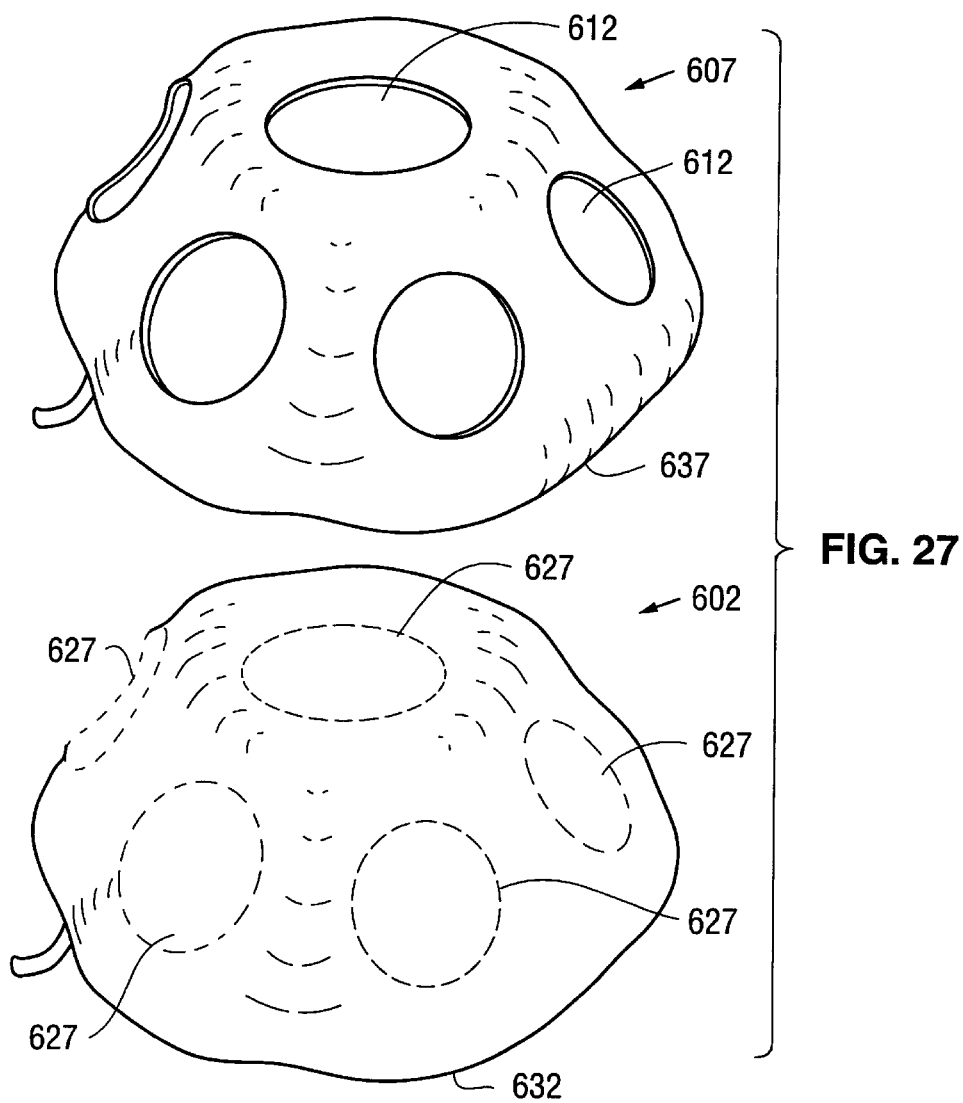
FIG. 27 is an exploded perspective view of the components of a substantially hemispherical Type IA retraction device illustrating the construction of such device according to the invention.
Figure 28:
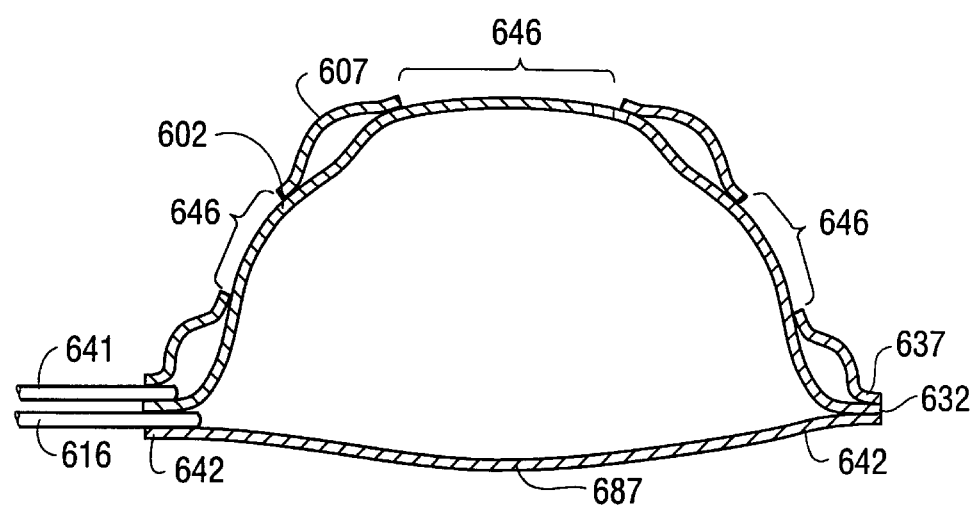
FIG. 28 is a cross sectional view of a substantially hemispherical Type IA retraction device.

Substantially full- or hemi-spherical, spheroidal, or ellipsoidal Type IA and Type II retraction devices can be made from curved pieces of plastic film. The construction according to the invention of a hemispherical Type IA retraction device from curved plastic film is illustrated in FIGS. 27 and 28. The method can easily be adapted to make a substantially spherical, spheroidal or ellipsoidal Type IA retraction device by interconnecting two envelope halves made according to the method to be described below using the method for joining envelope halves described above.

The main envelope 602, the additional envelope 607, and the bottom diaphragm 647 of the retraction device are all made of a relatively inelastic and tough film of a plastic such as Mylar®, polyethylene, or polyurethane. The preferred material is a polyethylene and nylon composite. The thickness of the main envelope 602 is typically from 0.5 to 5 mils (13 to 130 microns). In the preferred embodiment, the additional envelope 607 and the bottom diaphragm 647 are made from a film of the same thickness of the same plastic as the main envelope. However, in some applications it may be advantageous make the additional envelope and/or the bottom diaphragm from a film of a different thickness of the same plastic, or a film of the same or a different thickness of a different plastic.

A main envelope blank 602, an additional envelope blank 607 and a bottom diaphragm 647 are cut from a piece of film, preferably by die cutting. The envelope blanks are similar, except that holes 612 are cut in the additional envelope blank 607. The holes 612 are cut preferably by the same die that is used to cut the additional envelope blank 607. When the additional envelope is assembled with the main envelope blank, the holes 612 form the windows 646 (FIG. 28). In FIG. 27, holes 612 are shown as having a circular shape, but they could have other suitable shapes.

According to one aspect of the method, the main envelope blank 602 and the additional envelope blank 607 are stretched over the surface of a former. The surface of the former is the hemispherical, hemispheroidal, hemiellipsoidal, or other shape that it is desired to impart on the envelope blank. The surface of the former is heated and its temperature sufficiently high, and the envelope blank remains in contact with the surface of the former for sufficiently long a time, for the plastic film of the envelope blank to soften, such that when the envelope blank cools, it adopts the shape of the surface of the former. The surface of the former is cooled, the periphery of the envelope blank is trimmed to the periphery of the surface, and the envelope blank is removed from the former. An envelope blank can also be curved by blowing the envelope blank into a suitably-shaped, heated concavity, or by pressing the envelope blank between suitably-shaped, heated male and female dies.

An envelope half is made by laying the curved additional envelope blank 607 on the curved main envelope blank 602. The periphery of each hole 612 in the additional envelope blank 607 is attached to the main envelope blank 602, preferably by welding. Alternatively, a line of adhesive applied to the periphery each hole 612 can be used.

In an alternative method, an envelope half is made by laying the additional envelope blank 607 on the main envelope blank 602. The periphery of each hole 612 in the additional envelope blank 607 is attached to the main envelope blank 602, preferably by welding. Alternatively, a line of adhesive applied to the periphery of each hole 612 can be used. The resulting flat envelope half is then curved and trimmed around its periphery using one of the methods described above.

In either of the above methods, the main envelope blank and the additional envelope blank can cut using the same die, and the second chamber can be formed by attaching the additional envelope blank to the main envelope blank by welding or applying adhesive along the broken lines 627. This method produces a retraction device with a double layer of plastic film on the windows 646 (FIG. 28), which makes it somewhat less convenient to use.

A substantially hemispherical retraction device can be made by attaching the periphery 632 of the main envelope blank 602 to the periphery 637 of the additional envelope blank 607, and to the periphery 642 of the bottom diaphragm 647, preferably by welding, as shown in FIG. 28. Alternatively, a line of adhesive applied to the periphery of one or both the envelope halves and to the periphery 642 of the bottom diaphragm 647 can be used. A small part of the peripheries 632 and 637 is left unjoined. The additional inflation tube 641 is a piece of polyethylene tubing with an outside diameter in the range of 2.5 to 5 mm (0.1" to 0.2") and of suitable length. The distal end of the additional inflation tube 641 is fitted with a fitting (not shown) suitable for connecting it to a source of inflation gas (not shown). The proximal end of the additional inflation tube 641 is inserted into the unjoined part of the peripheries 632 and 637, and joining the periphery 632 to the periphery 637 is completed. Where the peripheries 632 and 637 contact the additional inflation tube 641, they are joined to the outer wall of the additional inflation tube to form a gas-tight seal.

A small part of the joint between the periphery 637 of the additional envelope blank 607 and the periphery 642 of the bottom diaphragm 647 is also left unjoined. The main inflation tube 616 is a piece of polyethylene tubing with an outside diameter in the range of 2.5 to 19.5 mm (0.1" to 0.77") and of suitable length. The distal end of the main inflation tube 616 is fitted with a port 651 that allows surgical instruments to be passed into the main inflation tube while maintaining inflation pressure in the main chamber of the retraction device. The port 651 also includes a fitting (not shown) suitable for connecting the port to a source of inflation gas (not shown). The proximal end of the main inflation tube 616 is inserted into the unjoined part of the peripheries 637 and 642, and joining the periphery 637 of the additional envelope blank 607 to the periphery 642 of the bottom diaphragm 647 is completed. Where the peripheries 637 and 642 contact the main inflation tube 616, they are joined to the outer wall of the main inflation tube such that a gas-tight seal is formed.

The methods described above for making curved envelope halves can also be used to make the envelope halves used in constructing a Type II retraction device.

We claim:

1. An inflatable retraction apparatus for retracting an organ inside a body to gain access to an adjacent tissue, the apparatus comprising:
    an inflatable chamber formed from a single thin envelope, the inflatable chamber capable of being collapsed for insertion into the body through an incision of the body and capable of being expanded to a predetermined shape for retracting the organ;
    an inflation mechanism adapted to selectively inflate the chamber to the predetermined shape, while the inflatable chamber is in place within the body, the inflation mechanism including at least one inflation tube attached to the inflatable chamber in fluid communication therebetween; and
    an inflatable maintaining lattice operatively enveloping the inflatable chamber and in operative association with the inflation mechanism, the inflatable maintaining lattice defining a plurality of single layered access windows around the inflatable chamber, the inflatable maintaining lattice being configured and adapted to maintain the inflatable chamber in substantially the predetermined shape after an aperture is pierced in at least one of the plurality of access windows of he inflatable chamber to provide access to the tissue.

2. The apparatus of claim 1 wherein the maintaining mechanism includes an additional chamber.

3. The apparatus of claim 2 wherein the additional chamber is attached to the inside of the inflatable chamber.

4. The apparatus of claim 2 wherein the additional chamber is attached to the outside of the inflatable chamber.

5. The apparatus of claim 2 wherein the inflation mechanism is adapted to selectively inflate the inflatable chamber and the additional chamber.

6. The apparatus of claim 2 wherein the inflatable chamber is adapted to be pierced, whereby apertures are formed to thereby provide access to the tissue.

7. The apparatus of claim 2 further including a tab element inside the main chamber for providing a point inside the inflatable chamber that can be gripped with a suitable gripping tool to change the position of the at least partly inflated apparatus.

8. The apparatus of claim 7 wherein the tab element is attached to the envelope.

9. The apparatus of claim 7 wherein the tab element constitutes part of the envelope.

10. The apparatus of claim 1 wherein the inflatable chamber is expandable to a polyhedral shape.

11. The apparatus of claim 1 wherein the inflatable chamber is expandable to a spherical shape.

12. The apparatus of claim 1 wherein the inflatable chamber is expandable to a ellipsoidal shape.

13. The apparatus of claim 1 wherein the inflatable chamber is expandable to a relatively flat shape.

14. The apparatus of claim 1 wherein the inflatable chamber includes a cage structure.

15. The apparatus of claim 1 wherein the maintaining mechanism includes an elastomeric window covering the aperture and providing access to the tissue.

16. The apparatus of claim 1 wherein the inflation mechanism is adapted for receiving a surgical instrument passed into the chamber from outside the body.

17. The apparatus of claim 1 wherein the aperture is adapted to receive the tissue for treatment.

18. The apparatus of claim 1, further including a suction means for providing drainage of the part of the body in which the apparatus is deployed, the suction means being attached to the part of the apparatus that is substantially lower-most when the apparatus is deployed in the body.

19. The apparatus of claim 18, wherein the suction means comprises an elongate tubular structure having a plurality of holes in its side-wall and two ends, at least one of the ends being adapted for connecting to a suction line.

20. The apparatus of claim 1 further including a flexible sheath means attachable to the envelope for providing a flexible passage to the chamber from outside the body.

21. An inflatable retraction apparatus for retracting an organ inside a body to gain access to an adjacent tissue, the apparatus comprising:

first and second inflatable chambers each formed from a thin envelope, the first and second inflatable chambers capable of being collapsed for insertion into the body through an incision of the body and capable of being expanded to a predetermined shape for retracting the organ, the second inflatable chamber enveloping the first inflatable chamber and defining a plurality of single layered windows therearound; and first and second inflating tubes in fluid communication with the first and second inflatable chambers, respectively, for independently inflating the first and second inflation chambers to the predetermined shape, wherein the second inflatable chamber maintains the first inflatable chamber in the predetermined shape following the formation of an aperture in at least one of the plurality of windows to provide access to the tissue.

22. The apparatus of claim 21, wherein the first inflatable chamber includes a wall portion having a piercable area formed thereon to provide access to tissue adjacent the apparatus.

23. The apparatus of claim 22, wherein the apparatus is adapted to maintain substantially the predetermined shape upon piercing of the piercable area.

24. The apparatus of claim 21, wherein the apparatus is adapted to receive a surgical instrument passed through at least one of the first and second inflatable chambers from outside the body.

25. The apparatus of claim 21 further including at least one tab for manipulating the location of the first and second inflatable chambers inside the body.

* * * * *